US006669842B1

(12) United States Patent
Armstrong

(10) Patent No.: US 6,669,842 B1
(45) Date of Patent: Dec. 30, 2003

(54) MACROCYCLIC ANTIBIOTICS AS SEPARATION AGENTS

(75) Inventor: Daniel Armstrong, Rolla, MO (US)

(73) Assignee: Curators of the University of Missouri, Columbia, MO (US)

(*) Notice: Subject to any disclaimer, the term of this patent is extended or adjusted under 35 U.S.C. 154(b) by 0 days.

(21) Appl. No.: 09/396,974

(22) Filed: Sep. 7, 1999

Related U.S. Application Data

(60) Division of application No. 09/187,369, filed on Nov. 6, 1998, now Pat. No. 5,964,996, which is a division of application No. 08/851,485, filed on May 5, 1997, now Pat. No. 5,874,005, which is a division of application No. 08/532,581, filed as application No. PCT/US95/02071 on Feb. 17, 1995, now Pat. No. 5,626,727, which is a continuation-in-part of application No. 08/198,409, filed on Feb. 22, 1994, now abandoned.

(51) Int. Cl.$^7$ .............................................. B01D 15/08
(52) U.S. Cl. .............................. 210/198.2; 210/502.1; 210/635; 210/656
(58) Field of Search ...................... 210/635, 656, 210/198.2, 502.1; 502/401, 403, 404; 435/174, 176, 178, 180

(56) References Cited

U.S. PATENT DOCUMENTS

| | | | |
|---|---|---|---|
| 3,607,700 A | 9/1971 | Tosteson | 204/195 |
| 4,216,083 A | 8/1980 | Dale | 252/428 |
| 4,290,893 A | 9/1981 | Hare | 210/656 |
| 4,460,474 A | 7/1984 | Blasius | 210/679 |
| 4,539,399 A | 9/1985 | Armstrong | 536/103 |
| 4,667,024 A | 5/1987 | Sitrin | 536/169 |
| 4,726,938 A | 2/1988 | Rollat | 423/215 |
| 4,943,375 A | 7/1990 | Bradshaw | 210/674 |
| 4,960,694 A | 10/1990 | Eckardt | 435/13 |
| 4,975,379 A | 12/1990 | Bradshaw | 436/77 |
| 5,030,352 A * | 7/1991 | Varady | 210/502.1 |
| 5,039,419 A | 8/1991 | Bradshaw | 210/502.1 |
| 5,064,944 A | 11/1991 | Armstrong | 536/1.1 |
| 5,100,585 A | 3/1992 | Horwitz | 252/631 |
| 5,104,547 A | 4/1992 | Cabrera et al. | 210/656 |
| 5,110,474 A | 5/1992 | Horwitz | 210/635 |
| 5,120,443 A | 6/1992 | Bruening | 210/638 |
| 5,154,738 A | 10/1992 | Armstrong | 55/67 |
| 5,175,110 A | 12/1992 | Bradshaw | 436/77 |
| 5,190,661 A | 3/1993 | Bruening | 210/670 |
| 5,194,133 A | 3/1993 | Clark et al. | 204/299 R |
| 5,198,429 A | 3/1993 | Konig | 514/58 |
| 5,200,041 A | 4/1993 | Simonet | 204/78 |
| 5,288,390 A | 2/1994 | Durante | 208/3 |
| 5,316,679 A | 5/1994 | Bruening | 210/670 |
| 5,338,454 A | 8/1994 | Duff | 210/635 |
| 5,356,538 A | 10/1994 | Wai | 210/634 |
| 5,626,757 A * | 5/1997 | Armstrong | 210/635 |
| 5,874,005 A * | 2/1999 | Armstrong | 210/635 |
| 5,964,996 A * | 10/1999 | Armstrong | 210/635 |

FOREIGN PATENT DOCUMENTS

WO 9400455 1/1994 ............ 210/198.2

OTHER PUBLICATIONS

DePedro, "Affinity Chromatography of Murein Precursors on Vancomycin—Sepharuse" FEMS Microbiology Letters 9 (1980) pp. 215–217.

"Affinity Chromatography", Chemical and Engineering News, Aug. 26, 1985, pp. 17–32.

(List continued on next page.)

Primary Examiner—Ernest G. Therkorn
(74) Attorney, Agent, or Firm—Muserlian, Lucas & Mercanti

(57) ABSTRACT

Macrocyclic antibiotics having ring structures with at least 10 members act as separation agents in crystallization, precipitation, filtration, electrophoresis, and chromatography. The macrocyclic antibiotics include ansamacrolides, macrolides, macrocyclic peptides, polyenes and derivatives thereof. The process has been found to be especially advantageous for separation of optical isomers by electrophoresis and chromatography.

10 Claims, 4 Drawing Sheets

OTHER PUBLICATIONS

D. Armstrong et al., "Use of a macrocyclic antibiotic as the chiral Selector for enantiomeric separations by TLC", *Journal of Liquid Chromatography*, vol. 17, No. 8, 1994, pp. 1695–1706.

D. Armstrong et al. "Macrocyclic antibiotics as a new class of chiral selectors for liquid chromatography" *Analytical Chemistry*, vol 66, No. 9, May 1, 1994, pp. 1473–1484.

D. Armstrong et al., Highly enantioselective capillary electrophoretic separations with dilute solutions of the macrocyclic antibiotic ristocetin A, *J. of Chromatography A*, vol. 689, Jan. 13, 1995, pp. 285–304.

D. Armstrong et al., "Use of a macrocylic antibiotic, Rifamycin B, and indirect deterection for the resolution . . . ", *Analytical Chemistry*, vol. 66, No. 10, May 15, 1994, pp. 1690–1695.

Y. Kojima et al., "Macrocyclic peptides, 3. Enantioface–differentiating abilities . . . ", *Die Makromolekulare Chemie*, vol. 10, No. 3, Mar. 1989, pp. 121–125.

H. Miyake et al., "Macrocyclic peptides, 8. Enantiomeric differentiations . . . " *Die Makromolekulare Chemie*, vol 194 No. 7, Jul. 1993 pp. 1925–1933.

* cited by examiner

TIME, MIN

MACROCYCLIC ANTIBIOTICS AS SEPARATION AGENTS

This application is a divisional of U.S. Ser. No. 09/187,369 filed Nov. 6, 1998, now U.S. Pat. No. 5,964,996 dated Oct. 12, 1999, which, in turn, was a divisional of U.S. Ser. No. 08/851,485 filed May 5, 1997, now U.S. Pat. No. 5,874,005; which, in turn, was a divisional of U.S. Ser. No. 08/532,581 filed Sep. 29, 1995, now U.S. Pat. No. 5,626,727 dated May 6, 1997; which, in turn, was an application pursuant to 35 USC 371 of PCT/US95/02071, filed Feb. 17, 1995, which, in turn, was a continuation-in-part of U.S. Ser. No. 08/198,409, filed Feb. 22, 1994, now abandoned.

Antibiotics are a class of chemical compounds which are produced by microorganisms; and capable, in a dilute solution, of inhibiting the growth of or destroying bacteria and other microorganisms. Today, some antibiotics are also produced synthetically. Chemically, antibiotics have a wide variety of structures and belong to various groups of compounds. Generally, antibiotics have three names, a chemical name, a generic name and a tradename. For example, tetracycline, generic name, is 4-dimethylamino-1,4,4a,5,5a,6,11,12a-octahydro-3,6,10,12,12a-pentahydroxy-6-methyl-1,11-dioxo-2-naphthocenecarboxamide, chemical name, and is sold under the tradenames Panmycin and Tetracyn. The generic name is generally preferred and will be used in the specification and claims.

A variety of methods are available for the separation of an individual component or chemical compound from fluids. Among these methods are distillation, extraction, crystallization, precipitation, filtration, electrophoresis and various chromatographic techniques.

Crystallization and precipitation are often batch operations which entail the addition of an agent to assist in the removal of a component from the fluid as a solid particle. Generally, the solid particles fall to the bottom or rise to the top of the fluid.

Filtration can be either a batch or continuous process and includes reverse osmosis or ultrafiltration and membrane permeation. Such processes entail the selective separation of components from a fluid due to the porosity of a filter. The filter itself can be either a fluid or a solid.

Chromatography, which also operates in either a batch or continuous mode, includes liquid chromatography, gas chromatography, paper chromatography and thin-layer chromatography. Chromatography is based on the differential distribution of components between two phases, a mobile phase and a stationary phase. The mobile phase is typically a gas or liquid while the stationary phase is typically a solid or a liquid. Separation occurs because the mobile phase is brought into contact with the stationary phase and caused to move past the stationary phase. Components in the mobile phase travel in the mobile phase at different rates depending on their affinity for the two phases.

Electrophoresis involves the motion of electrically charged particles in an electric field and comprises applying an electric field to a solution such that components in the solution move by means of the electric field. Electrophoresis can be done with free solutions in the presence of a gel, or in the presence of a chromatographic-like stationary phase (the later is sometimes referred to as electrochromatography). There are a variety of electrophoresis techniques. Electrophoresis can be performed in capillaries (capillary electrophoresis, CE), in tubes, in slabs, etc. Electrophoresis is typically only a batch process.

A number of these separation processes employ a chemical agent to assist in the separation of the compound which has been targeted for separation. Typically, these chemical agents, i.e. separation agents, are either added to the fluid phase so as to combine with the targeted compound and assist or effect the separation of the targeted compound, or the separation agent is fixed to a stationary phase and interacts with the targeted compound as it passes by the fixed separation agent thereby assisting or effecting the separation of the targeted compound.

When using crystallization or precipitation, the separation agent is typically added to the fluid such that it combines with the compound targeted for separation and causes precipitation or crystallization of a complex of the targeted compound and the separation agent. In a filtration process, the separation agents typically make up part of the filter by being either affixed to the filter or contained in the liquid which acts as the filter. In the fields of chromatography and electrophoresis, the separation agent is either attached to a solid support or dissolved in solution.

In the past, a number of different materials have been used as separation agents for chromatography and electrophoresis. Separation agents which have been affixed to the stationary phase in the field of chromatography include amino acids, derivatives of amino acids, proteins, cyclodextrins, derivatives of cyclodextrins and derivatives of linear or branched carbohydrates. In the field of electrophoresis, cyclodextrins and their derivatives have been used as separation agents with a wall immobilized chiral stationary phase. More often in the field of electrophoresis, the cyclodextrin is dissolved in free solution as are derivatives of cyclodextrin, amino acids, and soluble carbohydrates. The uses of separation agents in crystallization, precipitation, filtration, electrophoresis and chromatography is well-known and conventional.

The use of various separation agents and separation processes have been employed to separate optical isomers. The configuration of an optical isomer or chiral molecule generally determines its biological and pharmacological activity and effectiveness. It is not uncommon for one enantiomer of a chiral molecule to have a different activity from the other enantiomer. It is therefore essential to be able to separate and isolate the one enantiomer from the other. Separation agents used to separate optical isomers are often referred to as chiral selectors.

It has now been discovered that macrocyclic antibiotics can be used as separation agents in a wide variety of separation processes including crystallization, precipitation, filtration, chromatography and electrophoresis. In fact, in chromatography and electrophoresis processes, it has been found that the macrocyclic antibiotic of the present invention can separate certain optical isomers which were heretofore unable to be separated using known separation agents.

It is both surprising and unexpected that a macrocyclic antibiotic works in such a wide variety of separation processes because these macrocyclic antibiotics are so large. Heretofore only small antibiotics have been suggested for use as a separation agent, see U.S. Pat. No. 5,194,133 issued Mar. 10, 1993. The '133 patent does not disclose the use of antibiotics for separation of optical isomers.

It has been found that the macrocyclic antibiotic of the present invention can be used both as a stationary phase and as a mobile phase or solution additive for chromatography and electrophoresis. Specifically, it has been found that the macrocyclic antibiotic works as a stationary phase in chromatography and capillary electrophoresis and as a mobile phase or solution additive in capillary electrophoresis, thin-layer chromatography, and liquid chromatography. It has also been found that the macrocyclic antibiotic of the present invention when used as a stationary phase in chromatography is stable in both normal phase and reverse phase modes of operation. Furthermore, it appears that the selectivity of the stationary phase is different between the two chromatographic modes. Hence, the recognition mechanism in the reverse phase is not the same as the recognition mechanism in the normal phase. This phenomenon has been found in its enantioselectivity and its chiral recognition mechanism in both the normal and reverse phases for chromatography.

The macrocyclic antibiotic of the present invention, when used as a chiral selector in a stationary phase, has been found to have a greater stability and a higher capacity than the prior art protein based stationary phases. Unlike proteins, macrocyclic antibiotics are not denatured or irreversibly changed in enantioselectivity when used in normal phase mode.

It has also been found that closely related macrocyclic antibiotics when used as chiral selectors have somewhat similar but not identical selectivity. This means that if one macrocyclic antibiotic gives a partial separation then there is a very good chance that a closely related macrocyclic antibiotic will give a baseline separation under very similar and often identical operating conditions.

DESCRIPTION OF THE PREFERRED EMBODIMENTS

Figure 1:
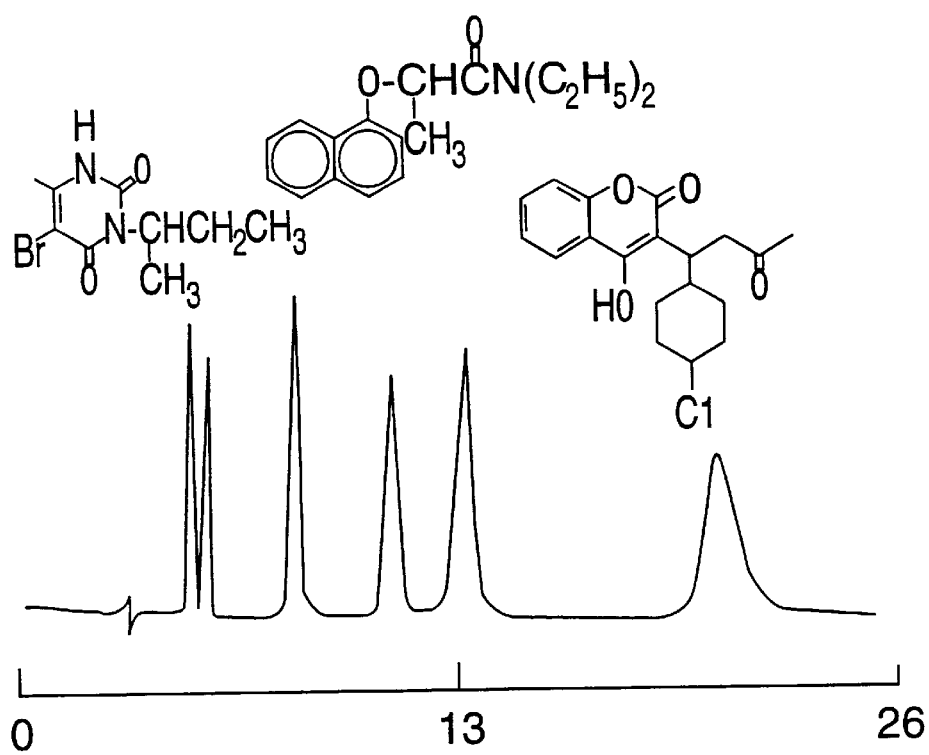
FIG. 1 illustrates the resolution of bromacil, devrinol and coumachlor enantiomers on a HPLC column in reverse phase using vancomycin bonded to a silica gel.

The macrocyclic antibiotic of the present invention is an antibiotic which has at least one macrocyclic ring structure. The term macrocyclic ring structure as used herein means that the ring structure contains at least about 10 members and more preferably at least about 15 members. The term member as used herein means a single atom. For example, a benzene ring is a six-membered ring while anthracene has three rings, each of which is a six-membered ring. Neither benzene nor anthracene has a macrocyclic ring. On the other hand, vancomycin, which is a macrocyclic antibiotic of the present invention, has ten rings, five of which are six-membered aromatic rings and not macrocyclic; two non-aromatic six-membered rings which are also not macrocyclic; and three rings with more than ten members which are macrocyclic rings in accordance with the present invention. The macrocyclic antibiotic of the present invention can have more than one macrocyclic ring, e.g. vancomycin. Good results have been found with a macrocyclic antibiotic having from 1 to 4 macrocyclic rings.

It is not completely understood why the macrocyclic antibiotic of the present invention works as a separation agent. It is thought that, with respect to the separation of optical isomers, the enantioseparation is made possible by a combination of several different mechanisms which allow the macrocyclic antibiotic to form a complex with a targeted component. These mechanisms include complexation, charge-charge interactions, hydrogen bonding, inclusion in a hydrophobic pocket, dipole stacking, steric interaction or combinations thereof. While all other chiral stationary phases avail themselves of the same types of interactions, a plurality of these mechanisms is not available in a single chiral selector and in relatively close proximity to one another. The plurality of interaction mechanisms of the present invention is made possible because the selectors of the present invention have more than one of these interaction mechanisms available and because the areas on the macrocyclic antibiotic where these interaction mechanisms are available are in close proximity to one another.

As is known to those of skill in the art, different separation agents have different degrees of effectiveness in separating components. That holds true for the macrocyclic antibiotics of the present invention. As is shown in the following examples, certain macrocyclic antibiotics are more effective at separating components than other macrocyclic antibiotics.

Derivatives of the macrocyclic antibiotic of the present invention can also be used as separation agents in accordance with the present invention so long as the interaction mechanisms of the macrocyclic antibiotic are not destroyed. It has been found that derivatization of the macrocyclic antibiotic changes its selectivity. Derivatization as used in the specification and claims means not only the addition of chemical components to the macrocyclic antibiotic but also derivatization where a portion of the macrocyclic antibiotic has been removed. Where a portion of the macrocyclic antibiotic has been removed, at least one of the macrocyclic ring structures must remain intact to allow the macrocyclic antibiotic dreivative to function as a separation agent. For instance, it is known that when certain macrocyclic antibiotics are bonded to a support matrix that a portion of the macrocyclic antibiotic is lost during the chmeical reaction. It is also known that there are methods which can be employed in order to prevent the loss of those portions of the macrocyclic antibiotic which are lost during the bonding reaction.

Polymers of macrocyclic antibiotics of the present invention can also be used as separation agents in accordance with the present invention.

The term macrocyclic antibiotic as used in the specification and claims means not only the macrocyclic antibiotic itself, but also derivatives of macrocyclic antibiotic as defined above and polymers of macrocyclic antibiotic.

Polymers of the macrocyclic antibiotic of the present invention can also be used as separation agents in accordance with the present invention.

Likewise, it has been found that the macrocyclic antibiotic of the present invention can be chemically bonded to a support and function as a separation agent. In bonding the macrocyclic antibiotic of the present invention, some of the structure of the macrocyclic antibiotic can be changed so long as the interaction mechanisms of the macrocyclic antibiotic are not destroyed.

Unlike other classes of separation agents, macrocyclic antibiotics comprise a large variety of structural types including macrocyclic polyene-polyols, ansa compounds (e.g. aliphatic bridged naphthohydroquinones), macrocyclic glycopeptides, peptides, peptide-heterocycle conjugates and so forth. In general, these compounds have molecular weights greater than 600 but less than 2,500 Daltons. There are acidic, basic and neutral types. Some cyclic antibiotics absorb strongly in the UV and visible spectral regions while others are fairly transparent.

Suitable macrocyclic antibiotics of the present invention may be generally classified by their similarity of chemical structure into the groups of: ansamacrolides, macroslides, macrocyclic peptides, which include glycopeptides, and polyenes. This list is not exhaustive and there are other antibiotics wherein the antibiotic has at least one macrocyclic ring which does not fit into one of these four categories. The preferred antibiotics are selected from the group of ansamacrolides and macrocyclic peptides, especially glycopeptides.

Ansamacrolides are a family of antibiotics characterized by an aliphatic ansa bridge which connects two non-adjacent positions on an aromatic nucleus. Ansamacrolides are generally divided into two groups based on their aromatic nucleus. One group contains a naphthoquinone and the other a benzoquinone nucleus. The naphthoquinoid ansamycins comprise the majority of the known ansamacrolides. Naphthoquinoid ansamycins which are useful in the present invention include streptovaricins, rifamycins, tolypomycins, halomicins, and naphthomycin. The benzoquinoid ansamacrolides which are useful in the present invention include geldanamycin and maytansinoids. The preferred ansamacrolide is rifamycin and especially rifamycin B.

Macrolides are a class of antibiotics having a macrocyclic ring forming the aglycone often as a 12-, 14- or 16-membered ring. Macrolides which are useful in the present invention include chalcomycin, methymycin, neomethymycin, erythromycin, megalomicin, picromycin, narbomycin, oleandomycin, triacetyloleandomycin, carbomycin, spiramycin, and tylosin.

Macrocyclic peptides that are useful in the present invention include sporidesmolides, capreomycin, ristomycin, cyclosporins, tyrocidine, triostins, gramicidins (gramicidin 5), tyrocidines, polymyxins, bacitracins, octapeptins, actinomycins, etamycins, vernamycins, enniatins, valinomycin, thiostrepton, teichomycin avoparcin, actaplanins and vancomycin. The preferred macrocyclic peptides are glycopeptides, and more especially teichomycin (teicoplanin), ristomycin, avoparcin, and vancomycin. Thiostrepton is also a preferred peptide.

The preferred glycopeptides have three (3) or four (4) fused rings. There are different numbers and types of sugars attached to the aglycone. Such preferred glycopeptides having these 3 or 4 fused rings include vancomycin, teichomycin, ristomycin, avoparcin and actaplanins. It is to be understood that teichomycin includes the different teichomycins such as:

| Teichomycin | R |
|---|---|
| $A_2$-1 | (Z)-4 decanoic acid |
| $A_2$-2 | 8-methylnonanoic acid |
| $A_2$-3 | n-decanoic acid |
| $A_2$-4 | 8-methyldecanoic acid |
| $A_2$-5 | 9-methyldecanoic acid |

It is also to be understood that avoparcin includes alpha-avoparcin and beta-avoparcin. Further, it is to be understood that actaplanins include the various types of actaplanins such as:

| actaplanin | $R_1$ | $R_2$ |
|---|---|---|
| A | mannosylglucose | mannose |
| $B_1$ | rhamnosylglucose | mannose |
| $B_2$ | glucose | mannose |
| $B_3$ | mannosylglucose | H |
| $C_1$ | rhamnosylglucose | H |
| G | glucose | H |

Polyenes have a large lactone ring which contains 3 to 7 double bonds. The preferred polyenes are amphotericin (amphotericin B), candicidin, candidin, dermostatin, fungichromin and nystatin.

Other antibiotics which do not fall into one of the four general categories listed above, but have a macrocyclic structure and are useful in the present invention include aplasmomycin, boromycin, enterobactin and bebeerine.

The most preferred macrocyclic antibiotics for use in the present invention are vancomycin, rifamycin, teicoplanin, avoparcin, and thiostrepton. Of the various rifamycins, rifamycin B is most preferred. Vancomycin is an amphoteric glycopeptide produced by the bacteria *Streptomycin orientallis*. Rifamycin B is one of the most common members of the family of rifamycin antibiotics and is obtained from the bacteria *Nocardia mediterranei*. Thiostrepton is obtained from the micro-organism *Streptomyces azureus*. Teichomycin is produced by the bacteria *Actinoplanes teichomyceticus*.

The macrocyclic antibiotics of the present invention can be obtained from any conventional source and are in many cases commercially available. Suitable derivatives of macrocyclic antibiotics for use in the present invention are made in any conventional manner using conventional reactants. Suitable derivatives include hydroxypropyl derivatives made with propylene oxide, acetyl derivatives made with acetic anhydride, (R)- or (S)-naphthylethylisocyanate derivatives, 3,5-dimethylphenylisocyanate derivatives, 2,6-dimethylphenylisocyanate derivatives, as well as others.

Polymers of the macrocyclic antibiotic which can be used in the present invention include homopolymers, derived from a single monomer, or mixed polymers, derived from more than one monomer. Such polymers are made in a conventional manner using conventional equipment. Typically, a crosslinking agent is used to chemically bond one macrocyclic antibiotic to another.

In stationary phase application, the macrocyclic antibiotic of the present invention is affixed to a support in a conventional manner. Suitably, the macrocyclic antibiotic of the present invention is affixed to a support by either coating a support or chemically bonding the macrocyclic antibiotic to the support.

The coating of the macrocyclic antibiotic of the present invention on a support is done in a conventional manner using conventional equipment. One suitable means for coating silica gel entails using macroporous spherical silica gel particles and silanizing these particles with a large excess of dichlorodiphenyl silane and triethylamine at refluxing temperature in toluene. The silanized silica gel is then coated with the macrocyclic antibiotic. The coated silica gel is used in a conventional column. In the case of coating a silica gel, polymers or copolymers of the macrocyclic antibiotic are preferred as they are not easily removed during separation procedures.

Figure 6:
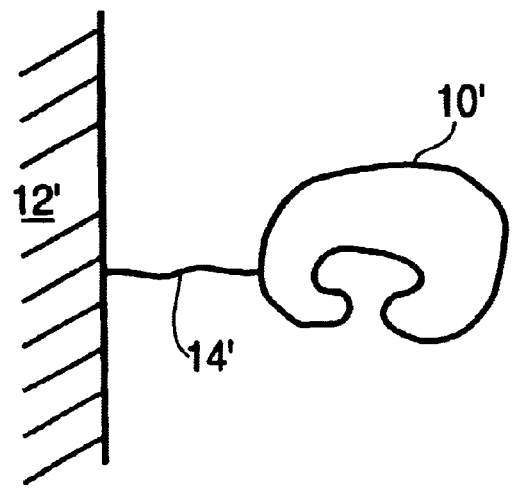
FIG. 6 illustrates a schematic of a macrocyclic antibiotic bonded to a support.

The macrocyclic antibiotic is chemically bonded to a support using conventional bonding chemistry, so long as it does not destroy the interaction mechanisms of the macrocyclic antibiotic which yields the separation mechanism of the present invention. The chemical bond between the support and the macrocyclic antibiotic forms a leash, bridge or spacer between the support and the macrocyclic antibiotic. The leash must be long enough so that the macrocyclic antibiotic is able to function as a separation agent, yet not so long as to dominate the separation. The order of reaction, e.g. support to leash then support-leash to macrocyclic antibiotic, will be dependent upon the chemistry of the support, leash and macrocyclic antibiotic. FIG. 6 illustrates a schematic of macrocyclic antibiotic 10'_ bonded to support 12'_ by linkage 14'_.

Suitable supports for making the stationary phase in accordance with the present invention include inorganic materials such as silica gel and alumina; synthetic polymeric materials such as polystyrenes, polyurethanes, polyvinyl alcohol and polyamides; natural materials such as agarose, cellulose, dextran and linear and branched amylose. A preferred support is silica gel.

In the case of chemically bonding a macrocyclic antibiotic to a silica gel, suitable bonding of the macrocyclic antibiotic to the support can be by way of a carboxylic acid terminated organosilane, an amine terminated oxysilane, epoxy terminated organosilanes and isocyanated terminated organosilanes. Suitable carboxylic acid terminated organosilanes include 10-(carbomethoxy)ethylmethyldichlorosilane and 2-(carbomethoxy)-ethyltrichlorosilane. Suitable amine terminated organosilanes include 3-amino-propyldimethylethoxysilane and 3-aminopropyltriethoxysilane. Suitable epoxy, terminated silanes include (3-glycidoxypropyl) trimethyloxysilane, 3-glycidoxypropyldimethylethoxysilane and 3-glycidoxypropyltriethoxysilane. Suitable isocyanated terminated organosilanes include 3-isocyanato-propyltriethoxysilane and 3-isocyanatopropyldimethylchlorosilane.

The linkage between the macrocyclic antibiotic and the leash includes ether, thioether, amine, amide, carbamate, urea, and hydrocarbon.

In order to form the stationary phase in accordance with the present invention using a carboxylic acid terminated or an amine terminated organosilane, dry silica is slurried with dry toluene and a solution of the organosilane in toluene is added dropwise over a period of time and refluxed with the toluene silica gel slurry. Refluxing is continued over a period of time at about 110° C. An amount of macrocyclic antibiotic is added along with an appropriate carbodiimide dehydrating agent. After allowing the mixture to react for a period of time, the stationary phase is filtered and washed.

In order to bond the macrocyclic antibiotic of the present invention to a silica gel and an isocyanate terminated organosilane, the macrocyclic antibiotic is reacted with a 2 or 3 molar excess of the organosilane in an anhydrous DMF. The reaction product is then added to a dry DMF slurry of silica gel wherein the weight ratio of modified macrocyclic antibiotic to silica gel is about 1:2. The solution is stirred and allowed to react for 20 hours at about 105° C. Subsequently, the reaction product is filtered and washed.

In order to form a stationary phase using the macrocyclic antibiotic of the present invention, silica gel and an epoxy terminated organosilane are reacted in toluene in a conventional manner, see for example U.S. Pat. No. 4,539,399.

Other suitable bonding chemistries between the silica gel or glass bead and the macrocyclic antibiotic of the present invention include making an α-aminopropyl silanized silica gel and then using a glutaraldehyde to attach an amino group from the macrocyclic antibiotic to the silanized silica gel. Such a process works where the macrocyclic antibiotic has an amino group.

In the case of a natural support such as agarose, cellulose, dextran or linear and branched amylose, the macrocyclic antibiotic is bonded to the support in a conventional manner using conventional equipment. See, for example, "Affinity Chromatography", Chemical and Engineering News, Aug. 26, 1985, pages 17–32.

The stationary phase employing the macrocyclic antibiotic of the present invention also includes encapsulation. Encapsulation of the macrocyclic antibiotic of the present invention is accomplished using a conventional process in a conventional manner to build a porous polymer cage around the macrocyclic antibiotic. Such porous polymer cages are formed as beads and are then used in columns. The porous cage allows the flow of material through the cage while preventing the escape of the macrocyclic antibiotic. In this way, the macrocyclic antibiotic of the present invention is able to function as a separation agent.

The macrocyclic antibiotic of the present invention is used in a conventional manner in a conventional separation process such as crystallization, precipitation, filtration, electrophoresis or chromatography.

In crystallization and precipitation, it is added as a separation agent to fluid in an amount effective to cause precipitation or crystallization of the targeted component, preferably in an amount greater than the amount of component in said fluid targeted for separation, more preferably about 2–10 times more.

In a filtration process, the macrocyclic antibiotic is affixed to a solid support or included as a component in the liquid filter. The macrocyclic antibiotic is used in the filtration process in a conventional manner with conventional equipment. The amount of macrocyclic antibiotic used in the filter is an amount effective to separate the targeted component.

In the processes of electrophoresis and chromatography, the macrocyclic antibiotic of the present invention is used in a conventional manner with conventional equipment as a mobile phase additive or affixed to a support.

These and other aspects of the present invention may be more fully understood by reference to the following examples.

EXAMPLE 1

This example illustrates making a stationary phase of macrocyclic antibiotics in accordance with the present invention.

In order to make a stationary phase, 1.0 g of the macrocyclic antibiotic was dried in vacuo over $P_2O_5$ at 100° C. for four hours. Dried macrocyclic antibiotic was then dissolved (using a stirring bar) with 100 ml of anhydrous N,N-dimethyl formamide (DMF) in a 500 ml, three-neck round bottom flask. The reaction was blanketed with dry $N_2$ gas. Dry $N_2$ gas was introduced through one neck and initially was allowed to sweep through the apparatus and escaped through the second neck which also was fitted with a thermometer using a standard two neck adapter. The third neck of the round bottom flask was equipped with a dropping funnel which had a pressure equalizing side tube. The flask was heated using a heating mantle. When the temperature of the solution reached 90–95° C., 520 μl of 3-isocyanatopropyltriethoxysilane which was dissolved in 20 ml of DMF was added dropwise (at the rate of 10–15 drops/min.) while stirring the flask. After adding the reagent, the reaction was stirred for 10 hours. These steps produced a macrocyclic antibiotic-bonded-to-the-organosilane. Next, 3.5 g of silica gel (spherical, 5μ, 100 Å pore size) was dried in vacuo at 100° C. over $P_2O_5$ for four hours. The dried silica gel was then added to the DMF solution of macrocyclic antibiotic-bonded-to-the-organosilane and stirred and heated to 105° C. and allowed to react for 20–24 hours. The mixture was then allowed to cool to room temperature, filtered and washed with DMF, methanol, toluene, methanol, water and methanol.

This procedure was employed for each of the macrocyclic antibiotics as listed in Table I below:

TABLE I

Vancomycin
Streptomycin
Rifamycin B
3,5 dimethylphenyl-derivitized vancomycin

EXAMPLE 2

This example illustrates the use of various immobilized macrocyclic antibiotics as separation agents in a stationary phase. In this example, liquid chromatography was employed as the separation process to separate optical isomers. The data from this example are reported in Table II below for running the column in reverse phase condition.

TABLE II

| Compounds[a] | $k^b$ | α | Mobile Phase[c] | pH | Column[d] |
|---|---|---|---|---|---|
| 1) Coumachlor | 3.27 | 2.0 | 10/90 | 4.1 | Van |
| 2) Warfarin | 1.98 | 1.70 | 10/90 | 7.0 | Van |
|  | 2.27 | 1.44 | 10/90 | 4.1 | Van |
| 3) Devrinol | 1.40 | 1.62 | 10/90 | 4.1 | Van |
| 4) 5-Methyl-5- | 0.38 | 1.41 | 10/90 | 7.0 | Van |
| phenylhydantoin | 0.24 | 1.36 | 10/90 | 4.1 | Van |
| 5) Proglumide | 1.17 | 1.40 | 10/90 | 7.0 | Van |
|  | 1.18 | 1.75 | 10/90 | 4.1 | Van |
| 6) α-(1-Aminoethyl)-4-hydroxybenzyl alcohol | 0.39 | 1.30 | 10/90 | 7.0 | Van |
| 7) Bendroflumethiazide | 1.58 | 1.25 | 10/90 | 7.0 | Van |
| 8) Bromacil | 0.67 | 1.21 | 10/90 | 7.0 | Van |
| 9) Idazoxan | 0.38 | 1.21 | 10/90 | 7.0 | Rif |
| 10) 5-Cyano-6-methoxy-3,4-dihydro-2-pyridone | 0.32 | 1.21 | 10/90 | 7.0 | Van |
| 11) Pyridoglutethimide | 0.84 | 1.20 | 10/90 | 7.0 | Van |
| 12) N-carbamyl-D,L-phenylalanine | 0.31 | 1.20 | 10/90 | 4.1 | Van |
| 13) Aminoglutethimide | 0.79 | 1.15 | 10/90 | 7.0 | Van |
| 14) N-benzoyl-alanine methyl ester | 0.47 | 1.15 | 10/90 | 4.1 | Van |
| 15) Coumafuryl | 0.68 | 1.15 | 10/90 | 7.0 | Van |
| 16) Dansyl-α-amino-n-butyric acid | 3.29 | 1.15 | 10/90 | 4.1 | Van |
| 17) Dansyl-aspartic acid | 3.00 | 1.15 | 10/90 | 4.1 | Van |
| 18) N-(3,5-dinitrobenzoyl)-phenylglycine | 1.55 | 1.15 | 10/90 | 4.1 | Van |
| 19) Thioridazine | 22.0 | 1.15 | 10/90 | 7.0 | Thio |
| 20) Dansyl-norleucine | 6.17 | 1.14 | 10/90 | 4.1 | Van |
| 21) 5-(4-Hydroxyphenyl)-5-phenylhydantoin | 0.78 | 1.14 | 10/90 | 7.0 | Van |
| 22) Dansyl-serine | 2.09 | 1.12 | 10/90 | 4.1 | Van |
| 23) Indapamide | 1.35 | 1.12 | 10/90 | 7.0 | Van |
| 24) Benzoin methyl ether | 0.80 | 1.11 | 10/90 | 7.0 | Van |
| 25) N-benzoyl-leucine | 1.90 | 1.10 | 10/90 | 4.1 | Van |

[a]The compounds in this table are listed in order of their α-values from highest to lowest.
[b]This is the k of the first eluted enantiomer.
[c]The mobile phase compositions indicated are the volume ratios of acetonitrile to 1% triethylammonium acetate buffer.
[d]The abbreviations for the columns are as follows: Van = vancomycin bonded stationary phase, Thio = Thiostrepton bonded stationary phase and Rif = rifamycin B bonded stationary phase.

In order to test the different chiral stationary phases, columns were packed with the stationary phases in a conventional manner. The columns were made of stainless steel and measured 25 cm in length and had an inside diameter of 0.44 cm. Either a Shimadzu LC 6A liquid chromatograph with UV detection (254 nm) and a C-R3A chromatopac data station or a Waters model 590 HPLC with a 745B data module was used with the column to obtain the data reported in Table II above. Each separation was carried out at a flow rate of 1.0 ml per minute and at room temperature (22° C.). The columns were run in reverse phase in a conventional manner using 5 µl of a dilute solution obtained from a solution of 10 µg dissolved in 1 ml concentrate. The chiral stationary phases were prepared in accordance with Example 1 above.

The separation factor, alpha, was a measurement of the separation between the eluted peaks. The greater the separation between the peaks, the greater the value of alpha. Mathematically, alpha is defined as the ratio of corrected retention times of the two peaks being compared, i.e.

$$\alpha = t'_2/t'_1 = (t_2-t_0)/(t_1-t_0)$$

where t'=corrected retention time, t=uncorrected time and $t_0$=retention time of an unretained compound. Traditionally, the longest retained peak time $t_2$ is put in the numerator so that alpha will be greater than 1. An alpha value of 1 means that there is no separation (the peaks co-elute).

The capacity factor of the first eluted enantiomer, k, is the ratio of the corrected retention time to the retention time of an unretained compound, i.e. $k=(t_1-t_0)/t_0$.

FIG. 1 shows the resolution of bromacil, devrinol and coumachlor enantiomers in the reverse phase mode of the vancomycin bonded phase column. This run was conducted using the apparatus and following the method of this example. The mobile phase consisted of a 10/90 mix of acetonitrile and 1% triethylammonium acetate buffer at a pH of 7.

It should be noted that enantiomers of 5-cyano-6-methoxy-3,4-dihydro-2-pyridene have never been reported to have been resolved using a chiral stationary phase.

EXAMPLE 3

This example illustrates the effect of pH on the separation of coumachlor and devrinol using a vancomycin stationary phase as prepared in Example 1 above. The separation process employed in this example was liquid chromatography. The mobile phase was the same as in Example 2 above, and the columns were run in the same manner as Example 2 above. The results of this experiment are reported in Table III below.

TABLE III

|  | Coumachlor | | | Devrinol | | |
|---|---|---|---|---|---|---|
| pH | k | α | Rs | k' | α | Rs |
| 7.6 | 1.00 | 1.69 | 1.6 | 1.15 | 1.80 | 3.2 |
| 6.2 | 1.21 | 1.64 | 2.1 | 1.16 | 1.77 | 3.3 |
| 5.5 | 2.00 | 1.60 | 2.7 | 1.36 | 1.76 | 3.5 |
| 4.5 | 3.00 | 1.64 | 4.1 | 1.46 | 1.70 | 3.6 |
| 3.6 | 1.65 | 2.42 | 3.9 | 1.19 | 1.41 | 3.7 |

The values of k and alpha are determined in the same manner as in Example 2 above. $R_s=2(t_2-t_1)/(w_1+w_2)$ where $w_1$ and $w_2$ are the baseline peak widths of the first and second eluted peaks respectively.

EXAMPLE 4

This example illustrates the effect of temperature on the separation of proglumide, 5-methyl-5-phenylhydantoin, and N-carbamyl-D,L-phenylalanine. The separation process employed in this example was liquid chromatography. A vancomycin stationary phase as prepared in Example 1 above was employed. The mobile phase was the same and the column was run in the same manner, reverse phase, as in Example 2 above. The pH of the mobile phase was 4.1. The results from this experiment are reported in Table IV below. The k, alpha and $R_s$ values are determined in the same manner as in Example 3 above.

Table IV shows that lowering the separation temperature increases the retention as well as the selectivity (i.e. alpha value). In most cases it also resulted in enhanced resolution ($R_s$). This means that the gain in selectivity (alpha) was not completely offset by the loss in efficiency from the decrease in mass transfer that often occurs at lower temperatures.

TABLE IV

| Temperature (° C.) | k | α | Rs |
|---|---|---|---|
| Proglumide | | | |
| 0 | 1.33 | 2.27 | 3.6 |
| 5 | 1.33 | 2.11 | 3.3 |
| 15 | 1.31 | 1.87 | 2.4 |
| 22 | 1.18 | 1.75 | 2.1 |
| 35 | 0.93 | 1.57 | 1.8 |
| 45 | 0.76 | 1.44 | 1.6 |
| 5-Methyl-5-phenylhydantoin | | | |
| 0 | 0.35 | 1.38 | 1.5 |
| 5 | 0.27 | 1.36 | 1.0 |
| 22 | 0.24 | 1.34 | 1.0 |
| 35 | 0.24 | 1.30 | 0.9 |
| 45 | 0.19 | 1.32 | 0.7 |
| N-Carbamyl-D,L-phenylalanine | | | |
| 0 | 0.51 | 1.39 | 1.5 |
| 5 | 0.39 | 1.34 | 1.3 |
| 15 | 0.38 | 1.23 | 1.0 |
| 22 | 0.31 | 1.20 | 0.8 |
| 35 | 0.27 | 1.11 | 0.7 |
| 45 | 0.22 | 1.00 | 0 |

EXAMPLE 5

This example illustrates the effect of flow rate on the separation of 3a, 5,6-tetrahydrosuccinimidol [3,4-b] acenaphthen-10-one. The separation process employed in this example was liquid chromatography. A column was packed with a vancomycin stationary phase as prepared in Example 1 above and the mobile phase was a 50:50 (by volume) mix of isopropanol and hexane. Except for the fact that the column was run on normal phase, the column was run as in Example 2 above. As shown in Table V below, mass transfer was minimized by lowering flow rate which enhanced resolution, while having no effect on alpha. Alpha and $R_s$ determined in the same manner as Example 4 above.

TABLE V

| Flow Rate ml/min | α | Rs |
|---|---|---|
| 0.50 | 1.31 | 1.28 |
| 0.75 | 1.31 | 1.19 |
| 1.00 | 1.27 | 1.14 |
| 1.50 | 1.30 | 1.13 |
| 2.00 | 1.29 | 1.11 |

EXAMPLE 6

This example illustrates the separation obtained from various racemic compounds using various columns as prepared in Example 1 above. The separation process employed in this example was liquid chromatography. Except for operating the columns in normal phase resolution, the compounds were separated in the same manner as Example 2 above. The chromatographic data are reported in Table VI below. Alpha and k were determined in the same manner as Example 2 above.

Figure 2:
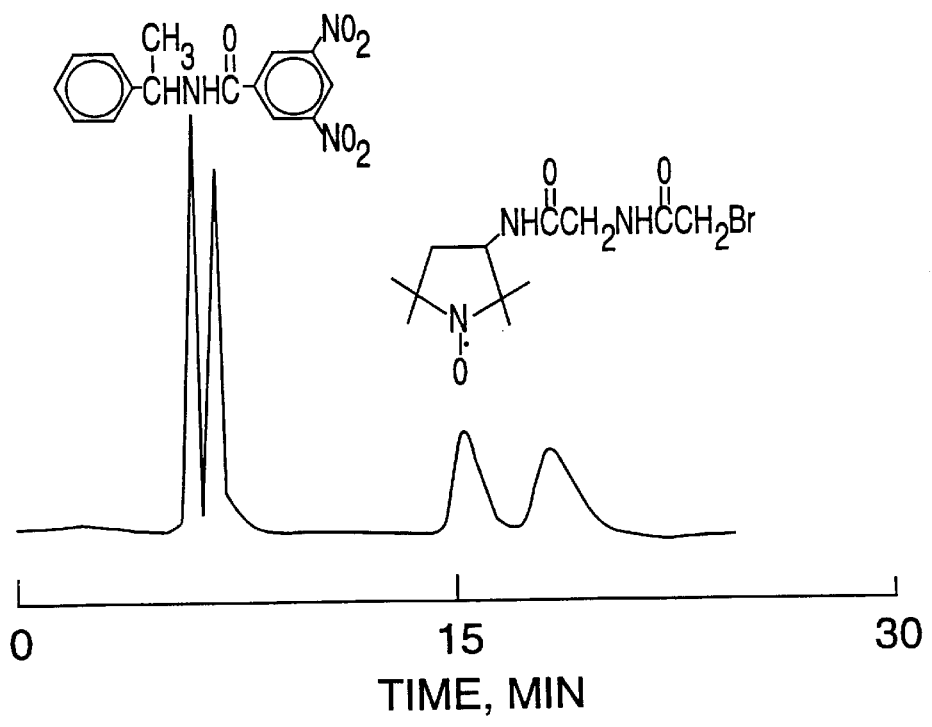
FIG. 2 illustrates the resolution of N-(3,5-dinitrobenzoyl)-alpha-methylbenzylamine and 3-[2-(2-bromacetamide) acetamide]-PROXYL enantiomers on a HPLC column in normal phase using vancomycin bonded to a silica gel.

FIG. 2 shows the resolution of N-(3,5-dinitrobenzoyl)-alpha-methylbenzylamine and 3-[2-(2-bromacetamido) acetamide]-PROXYL as reported in Table VI below.

It should be noted that the separation of 3-[2-(2-bromacetamido)acetamide]-PROXYL has not been achieved in any other chiral stationary phases heretofore.

It should also be noted that separations were only achieved with polar organic mobile phases for the last four compounds in Table VI below.

TABLE VI

| Compounds[a] | k[b] | α | Mobile Phase[c] | Column[d] |
|---|---|---|---|---|
| 1) 5-Methyl-5-phenyl-hydantoin | 2.50 | 1.67 | 50/50 | Van |
| 2) Mephobarbital | 0.58 | 1.62 | 50/50 | Van |
| 3) Hexobarbital | 0.75 | 1.61 | 50/50 | Van |
| 4) N-(3,5-dinitrobenzoyl) α-methylbenzylamine | 0.82 | 1.36 | 50/50 | Van |
| 5) Althiazide | 5.30 | 1.35 | 65/35 | Thio |
| 6) 1-Benzoyl-2-tert-butyl-3-methyl-4-imidazolidinone | 2.67 | 1.35 | 50/50 | Van |
| 7) N-(3,5-dintrobenzoyl-α-methylbenzylamine | 2.00 | 1.33 | 10/90 | Van |
| 8) 3-[2-(2-Bromoacetamido) acetamido]-PROXYL | 2.63 | 1.30 | 50/50 | Van |
| 9) Mephenytoin | 1.64 | 1.30 | 10/90 | Van |
| 10) Laudanosine | 2.37 | 1.13 | 10/90 | Rif |
| | 4.43 | 1.08 | 40/60 | Van |
| 11) Oxprenolol | 6.07 | 1.13 | 495/5/2/1[f] | Van |
| 12) Alprenolol | 6.07 | 1.05 | 495/5/2/1[f] | Van |
| 13) Propranolol | 8.17 | 1.04 | 495/5/2/1[f] | Van |

[a]The compounds in this table are listed in order of their α-values from highest to lowest (except for the last four compounds which use a different mobile phase).
[b]This is the-k of the first eluted enantiomer.
[c]The mobile phase composition represents the volume ratio of isopropanol to hexane.
[d]The abbreviations for the columns are as follows: Van = vancomycin bonded stationary phase, Thio = Thiostrepton bonded stationary phase and Rif = rifamycin B bonded stationary phase.
[e]This mobile phase composition represents the volume ratio of isopropanol/hexane/acetonitrile.
[f]These mobile phase compositions represent the volume ratios of acetonitrile/methanol/glacial acetic acid/triethylamine.

EXAMPLE 7

This example illustrates the use of a derivatized vancomycin as a stationary phase to separate various compounds using a liquid chromatography separation process. The stationary phase used in this example was made in accordance with Example 1 above. Except for the fact that the column was operated in normal phase, the column was operated in the same manner as in Example 2 above. Chromatographic data for this experiment are reported in Table VII below.

TABLE VII

| Compounds[a] | k[b] | α | Mobile Phase[c] | Column[d] |
|---|---|---|---|---|
| 1) Mephobarbital | 0.67 | 2.03 | 10/90 | DMP-Van |
| 2) 3a,4,5,6-Tetrahydro- | 1.46 | 1.50 | 50/50 | DMP-Van |

TABLE VII-continued

| Compounds[a] | k[b] | α | Mobile Phase[c] | Column[d] |
|---|---|---|---|---|
| succinimido[3,4-b] acenaphthen-10-one | | | | |
| 3) Hexobarbital | 0.91 | 1.45 | 10/90 | DMP-Van |
| 4) 1-Benzoyl-2-tert-butyl-3-methyl-4-imidazolidinone | 1.16 | 1.20 | 50/50 | DMP-Van |
| 5) Ftorafur | 3.65 | 1.25 | 50/50 | DMP-Van |
| 6) N,N'-Bis(α-methyl-benzyl) sulfamide | 3.47 | 1.15 | 10/90 | DMP-Van |
| 7) Hydroxyzine | 0.29 | 1.14 | 10/90 | DMP-Van |
| 8) Mephenytoin | 1.31 | 1.09 | 15/85 | DMP-Van |
| 9) Phensuximide | 3.11 | 1.09 | 15/85 | DMP-Van |
| 10) α-Carbethoxy-γ-phenyl-γ-butyrolactone | 0.70 | 1.08 | 10/90 | DMP-Van |
| 11) Glutethimide | 0.78 | 1.05 | 10/90 | DMP-Van |

[a]These compounds are listed in order of their α-values (from highest to lowest).
[b]This is the k of the first eluted enantiomer.
[c]The mobile phase compositions listed indicate the volume ratios of isopropanol to hexane.
[d]The abbreviation DMP-Van stands for the 3,5-dimethylphenylcarbamate derivatized vancomycin bonded CSP.

EXAMPLE 8

This example illustrates the effect of organic modifier concentrations on the separation of 5-methyl-5-phenolhydantoin enantiomers using a column packed with a vancomycin stationary phase as prepared in Example 1 above. The separation process employed in this example was liquid chromatography.

Figure 3:
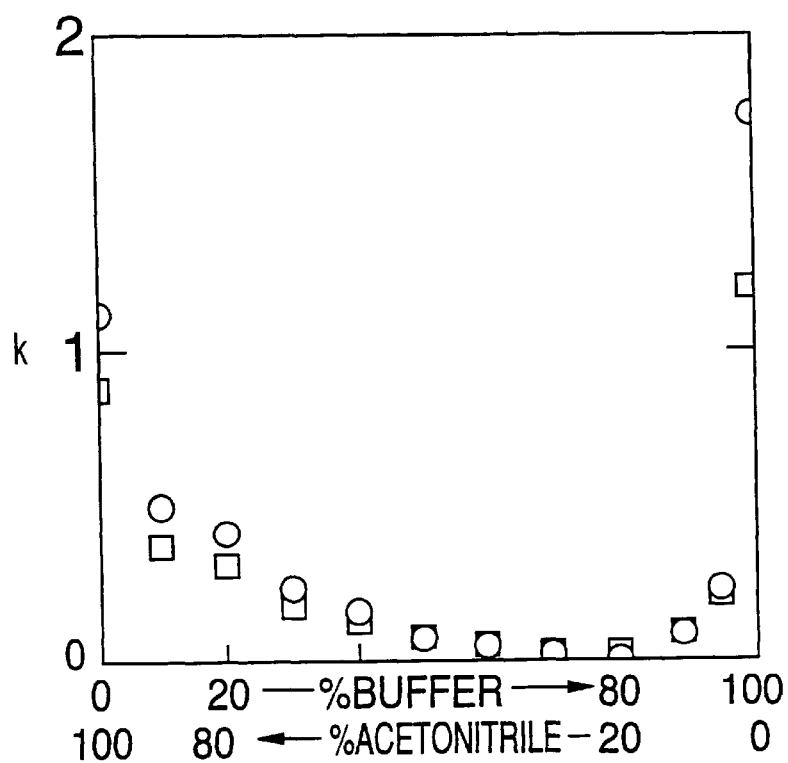
FIG. 3 illustrates the effect of an organic modifier on the separation of 5-methyl-5-phenolhydantoin enantiomer on a HPLC column in reverse phase using vancomycin bonded to a silica gel.

As shown in FIG. 3, increasing the concentration of acetonitrile modifier from 0 to 50% (by volume) caused the retention and enantioselectivity to decrease. At acetonitrile concentrations between 50 and 95% (by volume), there is little enantioselective retention and the analyte elutes near the dead volume of the column. In neat acetonitrile the retention increases and enantioselectivity returns.

FIG. 3 plots the reverse phase retention of the first eluted and second eluted enantiomers as a function of mobile phase composition. FIG. 3 refers to the first eluted enantiomer which is designated by a box while the second eluted enantiomer is designated by a blackened circle. The column was run in the same manner as in Example 2 above.

EXAMPLE 9

This example illustrates the effect of increasing the amount of analyte to be separated using liquid chromatography as the separation process. The separation agent employed in this example was a vancomycin stationary phase made in accordance with Example 1 above.

Figure 4:
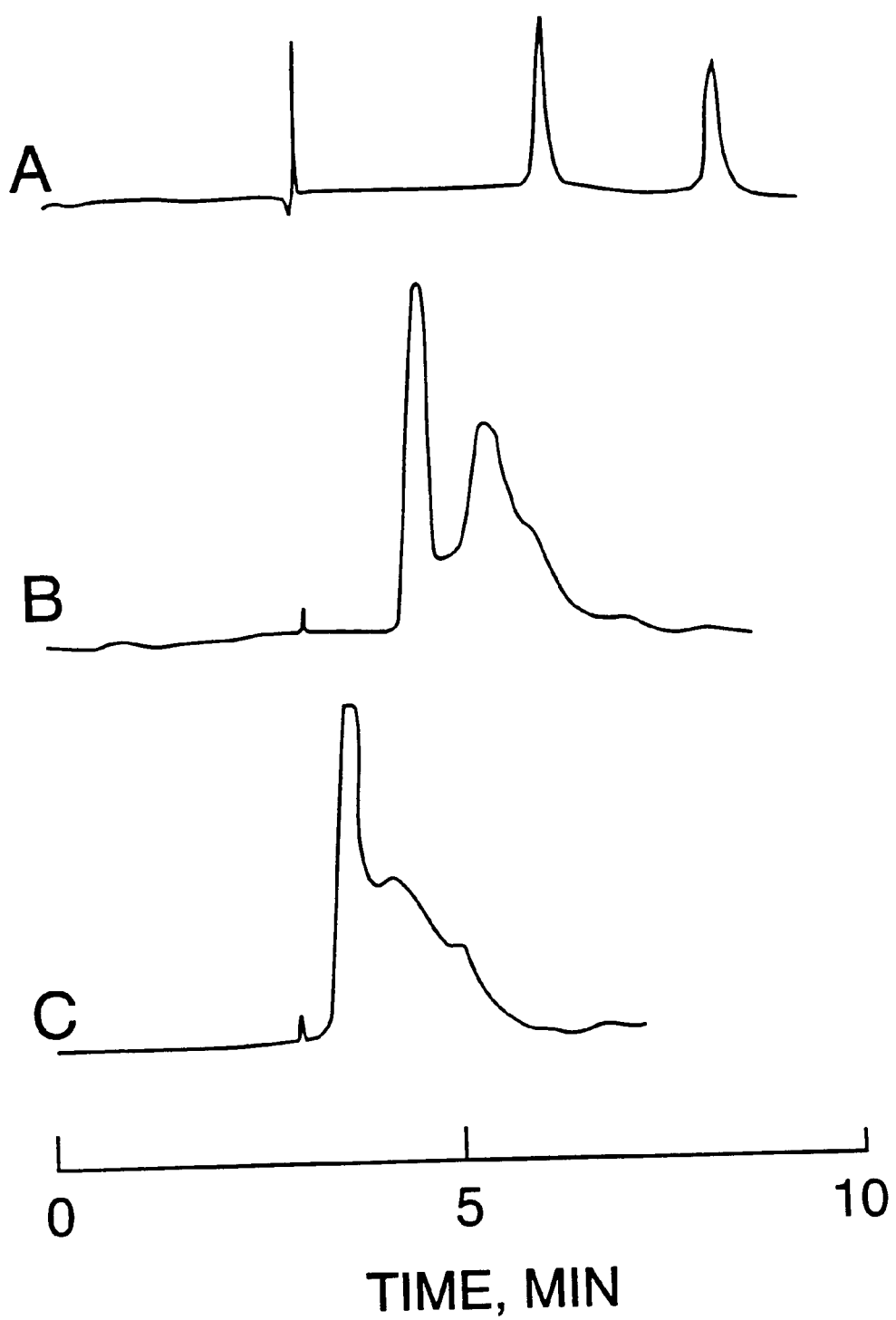
FIGS. 4A, 4B and 4C illustrate the effect on resolution of increased analyte on a HPLC column in reverse phase using vancomycin bonded to silica gel.

FIGS. 4A, 4B and 4C illustrate the different chromatograms for a mixture of 5-methyl-5-phenylhydantoin isomers. FIG. 4A illustrates a chromatogram for a 1 μg amount of the analyte; FIG. 4B illustrates a chromatogram for 500 μg of the analyte; and FIG. 4C illustrates a chromatogram for 1600 μg of the analyte. The column was run in the same manner as in Example 2 above with a mobile phase of neat acetonitrile.

EXAMPLE 10

This example illustrates the effect of adjusting the ratio of polar and non-polar organic solvents in a mobile phase with respect to the separation of compounds using liquid chromatography as the separation process. In this case, the organic solvents were hexane and isopropanol and the enantiomers which were resolved were from a mixture of methylphenylhydantoin isomers. The column employed had a vancomycin stationary phase as prepared in Example 1 above; and the column was run as in Example 2 above except it was run in normal phase mode.

Figure 5:
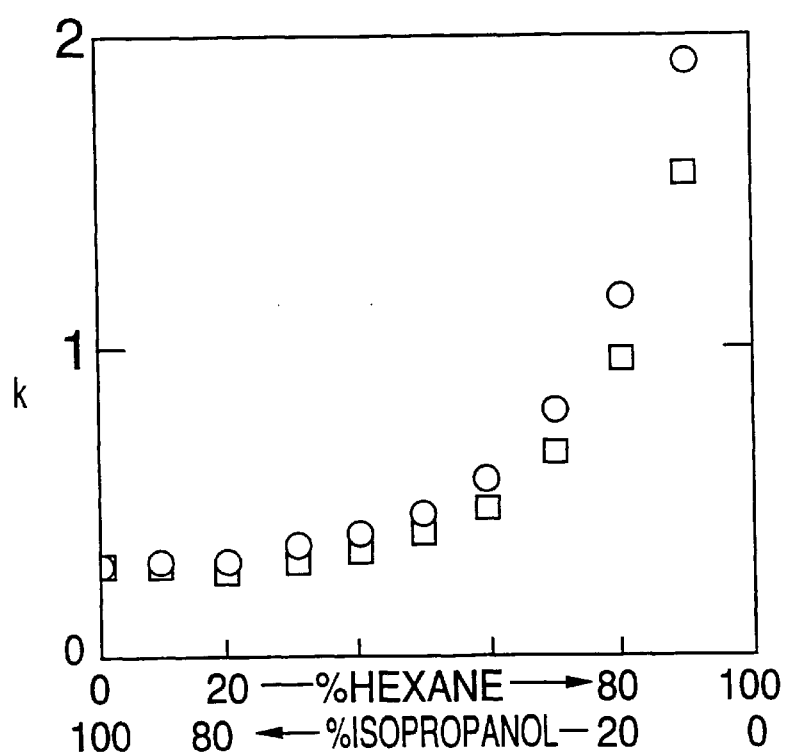
FIG. 5 illustrates the effect on resolution by adjusting the solvent, polar versus non-polar solvents, on a HPLC column in reverse phase using vancomycin bonded to silica gel.

FIG. 5 illustrates the results from this experiment. In FIG. 5 the square illustrates the first elute and the blackened circle the second elute of the enantiomers. It should be noted that only a polar organic phase was able to separate certain of the mixtures using this column, see specifically the last four enantiomers in Table VI of Example 6.

EXAMPLE 11

This example illustrates using rifamycin B to separate various compounds. The separation process employed in this example was electrophoresis, a stationary phase comprising a fused silica capillary having the macrocyclic antibiotic, rifamycin B, dissolved in solution for use in capillary electrophoresis. The results of the example are reported in Table VIII below.

TABLE VIII

| Compound | Rs | time[a] | μ(a)[b] | μ(e)[c] |
|---|---|---|---|---|
| Terbutaline | 3.1 | 62.5 | 5.8 | 1.8 |
| Isoproterenol | 2.3 | 63.4 | 5.7 | 1.8 |
| Bamethan | 1.9 | 60.1 | 6.0 | 2.1 |
| Metaproterenol | 1.8 | 59.5 | 6.0 | 2.1 |
| Synephrine | 1.7 | 53.3 | 6.7 | 2.8 |
| Metanephrine | 1.6 | 57.0 | 6.3 | 2.4 |
| Salbutamol | 1.5 | 59.5 | 6.0 | 2.1 |
| Epinephrine | 1.5 | 62.1 | 5.8 | 1.9 |
| Norphenylephrine | 1.5 | 54.6 | 6.6 | 2.7 |
| ±-Ephedrine ([1S,2R] and [1R,2S]) | 1.4 | 52.1 | 6.9 | 3.0 |

[a]Migration times are given in minutes.
[b]$\mu(a)$ is the apparent mobility in $cm^2 \cdot kV^{-1} \cdot min^{-1}$.
[c]$\mu(e)$ is the effective mobility in $cm^2 \cdot kV^{-1} \cdot min^{-1}$.

A fused silica capillary having a 50 μm inside diameter, 375 μm outside diameter, and 57.5 cm total length was obtained from Quadrex Corporation of New Haven, Conn. The capillaries were prepared by burning off the protective coating to form a window, inserting into a capillary holder and then conditioning the capillary with 0.5 normal potassium hydroxide.

A Quanta 4000 Capillary electrophoresis apparatus supplied by Waters and equipped with a 254 nm lamp was used for the tests. The distance to the detector in the capillary was 50 cm (effective capillary length). All analyzed samples were dissolved in distilled water at about 1 mg/mL, filtered with 0.45 μm nylon filters, and introduced into the capillary using electromigration injection for 5 seconds at 5 kV. The tests were run at a voltage of 8 kV and were carried out at room temperature (22° C.).

Enantiomeric resolutions, migration times and apparent and effective mobilities of the enantiomers were determined using 25 millimolar of rifamycin B in 40% 2-propanol, 60% 0.1 M phosphate buffer at a pH of 7.

Apparent mobility, $\mu(a)$, is determined by the following formula: $\mu(a)=(l)/(t \times E)=(l \times L)/(t \times V)$ wherein V is the applied voltage, l is the effective capillary length (to the detector), L is the total capillary length, t is the migration time as measured from the start of the run until detection, and E is the electronic field.

Effective mobility, $\mu(e)$, is determined by subtracting the mobility of a neutral particle, $\mu(EOF)$, from the apparent mobility, i.e. $\mu(a)-\mu(EOF)$. Apparent mobility and effective mobility are conventional measurements.

EXAMPLE 12

This example illustrates the effect of the concentration of rifamycin B as a separation agent using the separation process of electrophoresis. A column as taught in Example 11 above and the apparatus and method of Example 11 above were used for this example. Table IX below shows the migration times, apparent mobilities, effective mobilities and resolution of the enantiomers.

TABLE IX

| Compound | Rs | time | $\mu(a)$ | $\mu(e)$ |
|---|---|---|---|---|
| 15 mM Rifamycin B | | | | |
| Terbutaline | 1.1 | 37.8 | 9.5 | 2.4 |
| Norphenylephrine | 0.5 | 36.2 | 9.9 | 2.8 |
| Metoprolol | 0.2 | 39.0 | 9.2 | 2.1 |
| 20 mM Rifamycin B | | | | |
| Terbutaline | 1.5 | 41.7 | 8.6 | 2.0 |
| Norphenylephrine | 0.7 | 39.6 | 9.1 | 2.4 |
| Metoprolol | 0.3 | 42.2 | 8.5 | 1.9 |
| 25 mM Rifamycin B | | | | |
| Terbutaline | 2.0 | 48.6 | 7.4 | 1.7 |
| Norphenylephrine | 0.8 | 45.6 | 7.9 | 2.2 |
| Metoprolol | 0.4 | 49.2 | 7.3 | 1.6 |

The migration time is given in minutes while the apparent mobility, $\mu(a)$, and effective mobility, $\mu(e)$, are reported in $cm^2.kV^{-1}.min^{-1}$. All separations were done with a buffer of 70% 0.1 M phosphate and 30% 2-propanol with a pH of 7 at the indicated amounts of rifamycin B.

As can be seen from Table IX above, increasing the concentration of rifamycin B tends to increase the migration times somewhat as a result of small decreases in electrophoretic mobility. As shown in Table IX, this significantly enhances the enantiomeric resolution.

EXAMPLE 13

This example illustrates the effect of pH on rifamycin B as a separation agent in electrophoresis. The apparatus and method of Example 11 above was used in this example. All separations were done using 25 mM rifamycin B in 70% 0.1 M phosphate and 30% 2-propanol. The results of this experiment are reported in Table X below.

TABLE X

| Compound | Rs | time | $\mu(a)$ | $\mu(e)$ | Rs | time | $\mu(a)$ | $\mu(e)$ |
|---|---|---|---|---|---|---|---|---|
| | pH 5.2 | | | | pH 6.0 | | | |
| Terbutaline | 0.6 | 55.0 | 6.5 | 2.6 | 1.8 | 42.6 | 8.4 | 2.5 |
| Norphenylephrine | 0.3 | 45.0 | 8.0 | 3.3 | 0.9 | 41.1 | 8.7 | 2.7 |
| Metoprolol | 0.2 | 58.0 | 6.2 | 2.3 | 0.4 | 48.6 | 7.4 | 1.5 |
| | pH 7.0 | | | | pH 8.0 | | | |
| Terbutaline | 2.0 | 48.6 | 7.4 | 1.7 | 1.4 | 49.2 | 7.3 | 1.3 |
| Norphenylephrine | 0.8 | 45.6 | 7.9 | 2.2 | 0.4 | 46.2 | 7.8 | 1.6 |
| Metoprolol | 0.4 | 49.2 | 7.3 | 1.6 | 0.3 | 37.4 | 9.6 | 1.5 |
| | | | | | pH 9.0 | | | |
| Terbutaline | | | | | 0.8 | 34.0 | 10.5 | 1.2 |
| Norphenylephrine | | | | | 0.0 | 34.8 | 10.3 | 0.5 |
| Metoprolol | | | | | 0.0 | 32.8 | 11.0 | 1.3 |

The effect of pH on both migration time and enantiomeric resolution is more complicated with rifamycin B than with other separation agents such as cyclodextrin. This is because rifamycin B has ionizable functional groups. Therefore, pH not only affects the electro-osmotic flow, but also the charge and molecular recognition properties of both the analyte and the chiral selector. Clearly, all of these factors must be balanced in order to maximize resolution. As has been shown in Table X, the best resolution for racemic amino-alcohols is obtained at pH levels near 7, which produces intermediate electrophoretic mobilities and migration times.

EXAMPLE 14

This example illustrates the effect of organic additives on the separation of enantiomers with rifamycin B using electrophoresis. All separations were done using 20 mM rifamycin B in a solution of 70% 0.1 M phosphate and 30% of the organic additives as listed in Table XI below. The pH of the solution containing the rifamycin B was 7. The organic additives are listed in Table XI below. All other aspects of this example were conducted in accordance with Example 11 above.

TABLE XI

| Compound | Rs | time | $\mu(a)$ | $\mu(e)$ | Rs | time | $\mu(a)$ | $\mu(e)$ |
|---|---|---|---|---|---|---|---|---|
| | Acetonitrile | | | | Methanol | | | |
| Terbutaline | 0.3 | 18.6 | 19.3 | 5.0 | 0.4 | 30.0 | 12.0 | 3.1 |
| Norphenylephrine | 0.0 | 17.8 | 20.2 | 5.9 | 0.0 | 27.3 | 13.2 | 4.2 |
| Metoprolol | 0.0 | 18.8 | 19.1 | 4.8 | 0.0 | 30.3 | 11.9 | 2.9 |
| | Ethanol | | | | 1-Propanol | | | |
| Terbutaline | 0.8 | 41.4 | 8.7 | 2.3 | 1.4 | 34.2 | 10.5 | 2.2 |
| Norphenylephrine | 0.2 | 39.3 | 9.1 | 2.8 | 0.4 | 31.8 | 11.3 | 2.7 |
| Metoprolol | 0.2 | 43.5 | 8.3 | 2.0 | 0.2 | 33.9 | 10.6 | 2.0 |
| | 2-Propanol | | | | 2-Propanol + 0.5% methyl t-butyl ether | | | |
| Terbutaline | 1.5 | 41.4 | 8.6 | 2.0 | 1.4 | 51.0 | 7.1 | 1.1 |
| Norphenylephrine | 0.7 | 39.6 | 9.1 | 2.4 | 0.7 | 47.1 | 7.6 | 1.6 |
| Metoprolol | 0.3 | 40.2 | 8.5 | 1.9 | 0.3 | 49.8 | 7.2 | 1.0 |

As can be seen in Table XI, the organic modifiers have a profound effect on enantiomeric resolution, electrophoretic mobilities and migration times. The addition of 2-propanol to the solution tends to enhance enantiomeric resolution relative to equivalent volume percents of other organic additives. Although the 2-propanol also tends to produce longer migration times and lower electrophoretic mobilities, some of the organic modifiers that produce comparable or longer migration times did not produce equivalent enantioselectivity separations.

EXAMPLE 15

This example illustrates the effect of 2-propanol concentrations on separation of enantiomeric compounds using electrophoresis as the separation process. The apparatus and method as described in Example 11 above was used in order to obtain the chromatographic data in Table XII below. All separations were done using a 0.1 M phosphate at a pH of 7 at the indicated volume percent of 2-propanol. The amount of rifamycin B used in each of the separations is also indicated below in Table XII.

TABLE XII

| Compound | Rs | time | $\mu(a)$ | $\mu(e)$ |
|---|---|---|---|---|
| (A) 20 mM Rifamycin B | | | | |
| 10% 2-Propanol | | | | |
| Terbutaline | 0.0 | 21.0 | 17.1 | 3.4 |
| Norphenylephrine | 0.0 | 18.9 | 19.0 | 5.1 |

TABLE XII-continued

| Compound | Rs | time | μ(a) | μ(e) |
|---|---|---|---|---|
| Metoprolol | 0.0 | 20.7 | 17.4 | 3.3 |
| 20% 2-Propanol | | | | |
| Terbutaline | 0.5 | 29.4 | 12.2 | 2.8 |
| Norphenylephrine | 0.0 | 27.3 | 13.2 | 3.7 |
| Metoprolol | 0.0 | 30.6 | 11.7 | 2.4 |
| 30% 2-Propanol | | | | |
| Terbutaline | 1.5 | 41.7 | 8.6 | 2.0 |
| Norphenylephrine | 0.7 | 39.6 | 9.1 | 2.4 |
| Metoprolol | 0.3 | 42.2 | 8.5 | 1.9 |
| (B) 25 mM Rifamycin B | | | | |
| 30% 2-Propanol | | | | |
| Terbutaline | 2.0 | 48.6 | 7.4 | 1.7 |
| Norphenylephrine | 1.0 | 45.6 | 7.9 | 2.2 |
| Metoprolol | 0.5 | 49.2 | 7.3 | 1.6 |
| 40% 2-Propanol | | | | |
| Terbutaline | 3.1 | 62.5 | 5.8 | 1.8 |
| Norphenylephrine | 1.5 | 54.6 | 6.6 | 2.7 |
| Metoprolol | 0.8 | 62.1 | 5.8 | 1.9 |

As can be seen above, the data in Table XII shows that a low 2-propanol concentration has no enantio-resolution of any of the analyte tested. As the concentration of organic modifier increased, the electrophoretic mobilities decreased, the migration times increased, the electro-osmotic flow decreased, and the enantio-separation is enhanced.

EXAMPLE 16

This example illustrates the effect of sodium chloride on the separation of enantiomers with rifamycin B. All separations were done using a 25 mM rifamycin B solution in 70% 0.1 M phosphate and 30% 2-propanol solution at a pH of 6. The apparatus and method of Example 11 above was employed for obtaining the chromatographic data reported in Table XIII below.

TABLE XIII

| Compound | Rs | time | μ(a) | μ(e) |
|---|---|---|---|---|
| 0 M NaCl | | | | |
| Terbutaline | 1.8 | 42.6 | 8.4 | 2.5 |
| Norphenylephrine | 0.9 | 41.1 | 8.7 | 2.7 |
| Metoprolol | 0.4 | 48.6 | 7.4 | 1.5 |
| 0.05 M NaCl | | | | |
| Terbutaline | 1.4 | 52.2 | 6.9 | 2.0 |
| Norphenylephrine | 0.8 | 45.9 | 7.8 | 2.9 |
| Metoprolol | 0.3 | 55.2 | 6.5 | 1.6 |
| 0.10 M NaCl | | | | |
| Terbutaline | 1.1 | 54.3 | 6.6 | 1.6 |
| Norphenylephrine | 0.7 | 46.2 | 7.8 | 2.8 |
| Metoprolol | 0.2 | 57.6 | 6.2 | 1.3 |

As can be seen, increasing the ionic strength uniformly decreased enantiomeric resolution even though migration time increased and electrophoretic mobilities decreased. As can be seen, increasing the ionic strength produced very similar effects to increasing the concentration of 2-propanol with respect to migration times and electrophoretic mobilities. In both cases, migration times increased, while electrophoretic mobilities decreased.

EXAMPLE 17

This example illustrates the effect of buffer concentration and buffer composition on the separation of enantiomers with rifamycin B in electrophoresis. Using the apparatus and method of Example 11 above, all separations were done with 20 mM rifamycin B and 70% 0.1 aqueous buffer as indicated in Table XIV below and 30% 2-propanol. As shown in Table XIV below, the optimum concentration of phosphate buffer appears to be 0.1 M.

TABLE XIV

| Compound | Rs | time | μ(a) | μ(e) | Rs | time | μ(a) | μ(e) |
|---|---|---|---|---|---|---|---|---|
| | 0.05 M Phosphate | | | | 0.10 M Phosphate | | | |
| Terbutaline | 1.0 | 38.1 | 9.4 | 2.2 | 1.5 | 41.7 | 8.6 | 2.0 |
| Norphenylephrine | 0.6 | 34.5 | 10.0 | 3.0 | 0.7 | 39.6 | 9.1 | 2.4 |
| Metoprolol | 0.2 | 37.8 | 9.5 | 1.8 | 0.3 | 42.2 | 8.5 | 1.9 |
| | 0.15 M Phosphate | | | | 0.05 M Boric Acid + 0.05 M Phosphate | | | |
| Terbutaline | 1.0 | 45.0 | 8.0 | 2.0 | 1.1 | 42.6 | 8.4 | 1.9 |
| Norphenylephrine | 0.5 | 42.3 | 8.5 | 2.5 | 0.2 | 35.0 | 10.3 | 3.0 |
| Metoprolol | 0.2 | 45.3 | 7.9 | 1.8 | 0.1 | 37.5 | 9.6 | 1.9 |

EXAMPLE 18

This example illustrates the use of vancomycin to separate a variety of chiral compounds using capillary electrophoresis.

The apparatus and method of Example 11 above was used with a fused silica capillary measuring 25 cm to detector (32.5 cm total) in length and having an inside diameter of 50 micrometers. Separations were obtained by using 5 mM vancomycin in a 0.1 M phosphate buffer.

In one series of runs, amino acid derivatives of N-hydroxy-succinimidyl-6-amino quinoline carbamate (AQC) were separated. In each run the voltage was +5 kV and the pH of the buffer was 7.0. One run entailed separating a D,L mix of an α-amino-n-butyric acid derivatized with AQC and the other run entailed separating a D,L mix of a phenylalainine derivatized with AQC. Separation of the enantiomers was obtained in each case and the respective $R_s$ values were 9.71 and 8.07.

Other runs were made with AQC derivatives of the protein amino acids and those of many other amino acids. In each case vancomycin was able to resolve the enantiomers. The average resolutions of 5–10 were achieved.

In another series of runs, enantiomers of dansyl amino acid derivatives were separated. In the first two runs the voltage was +5 kV and the buffer had a pH of 4.9. The first run separated a mix of dansyl-D,L-methionine while the second run separated a mix of dansyl-D,L-α-amino-n-butyric acid. Separation of the enantiomers was obtained in each case and the respective $R_s$ values were 19.7 and 20.0. In a third run a mix of dansyl-D,L-glutanic acid was resolved using a buffer at a pH of 6.0 and a voltage of −5 kV.

Other runs were made with commercially available racemic dansyl derivatized amino acids. Resolution of the enantiomers was achieved with resolutions as high as 15–20 obtained.

In yet another run a mix of N-2,4-dinitrophenyl-D,L-glutanic acid was resolved using a buffer at a pH of 6.0 and a voltage of −5 kV. Other N-2,4-dinitrophenyl amino acid derivatives were also resolved. These other derivatives included those of ethionine, citrulline, serine, methionine, norleucine, norvaline, α-amino-n-butyric acid and α-amino-n-caprylic acid.

Other runs were made using vancomycin to separate various chiral compounds using the electrophoresis process and apparatus of this example. The N-3,5-dinitrophenyl derivatives of ethionine, leucine, serine, phenylalanine, tryptophan, methionine, norleucine, norvaline, and α-amino-n-butyric acid were resolved. Respective D,L mixes of the alanine, valine, leucine, phenylalanine, methionine and phenylglycine derivatized with N-benzoyl groups and 3,5-dinitrobenzoyl groups were resolved. Various D,L mixes of N-carbobenzyloxy amino acids were resolved. Various D,L mixes of N-phthalyl and N-phthalylglycoyl amino acids were resolved. Enantiomers of ibuprofen, indoprofen, flurbiprofen, carprofen, suprofen, fenoprofen and p-hydroxymandelic acid were resolved. Additionally, warfarin and coumachlor, which are neutral compounds, were also resolved.

EXAMPLE 19

This example illustrates the use of a macrocyclic antibiotic of the present invention for separation of chiral molecules using a thin-layer chromatographic technique.

The macrocyclic antibiotic, vancomycin, was used as a chiral mobile phase additive for the thin-layer chromatographic (TLC) resolution of 6-aminoquinolyl-N-hydroxysuccinimidyl carbamate (AQC) derivatized amino acids, racemic drugs and dansyl amino acids. Excellent separations were achieved for most of these compounds in the reversed phase mode. Both the nature of the stationary phase and the composition of the mobile phase strongly influenced enantiomeric resolution. The best results were obtained using diphenyl stationary phases. Acetonitrile was the organic modifier that produced the most effective separations with the shortest development times. The results from the various runs are reported in Table XV below.

TABLE XV

| | Compound | $R_{f1}$ | $R_{f2}$ | α | $R_s$ | Conc. (M) | Mobile Phase[a] |
|---|---|---|---|---|---|---|---|
| 1. | Coumachlor | 0.14 | 0.20 | 1.4 | 2.5 | 0.05 | 4/6/0 |
| 2. | Indoprofen | 0.58 | 0.63 | 1.1 | 1.6 | 0.05 | 4/6/0 |
| 3. | Warfarin | 0.04 | 0.06 | 1.5 | 1.2 | 0.04 | 2/10/0 |
| 4. | Bendroflume-thiazide | 0.02 | 0.06 | 3.0 | 1.8 | 0.05 | 0.5/8.5/1 |
| 5. | AQC[b]-α-amino phenylacetic acid | 0.13 (L) | 0.16(D) | 1.2 | 1.9 | 0.025 | 2/10/0 |
| 6. | AQC[b]-3-amino-3-phenylpropinic acid | 0.12<br>0.11 | 0.18<br>0.19 | 1.5<br>1.7 | 2.5<br>2.2 | 0.4<br>0.025 | 2/10/0<br>2/10/0 |
| 7. | Dansyl-tryptophan | 0.01 (L) | 0.03(D) | 3.0 | 1.3 | 0.04 | 2/10/0 |
| 8. | Dansyl-valine | | | | | | |
| 9. | AQC[b]-leu-leu | 0.06 (L) | 0.10(D) | 1.7 | 1.5 | 0.04 | 2/10/0 |
| 0.04 M, 2/10/0[a] | $R_{f1}$ (D-L) 0.03 | $R_{f3}$ (L-D) 0.10 | $α_1$ (DLLD) 3.3 | | | $R_{S1}$ (DLLD) 5.0 | |
| | $R_{f2}$ (L-L) 0.04 | $R_{f4}$ (D-D) 0.24 | $α_2$ (LDLD) 6.0 | | | $R_{S2}$ (LDLD) 11.6 | |
| (0.02 M, 1.5/4.5/0)[a] | $R_{f1}$ (D-L) 0.17 | $R_{f3}$ (L-D) 0.22 | $α_1$ (DLLD) 1.3 | | | $R_{S1}$ (DLLD) 4.5 | |
| | $R_{f2}$ (L-L) 0.18 | $R_{f4}$ (D-D) 0.42 | $α_2$ (LDLD) 2.3 | | | $R_{S2}$ (LDLD) 18.5 | |

[a]mobile phase compositions listed indicate the volume ratios of acetonitrile/0.6 M NaCl/1% triethylammonium acetate buffer (pH = 4.1).
[b]AQC stands for 6-aminoquinolyl-N-hydroxysuccinimidyl carbamate, a fluorescent-tagging-agent (see Experimental section).

All racemic analytes, the vancomycin, all dansyl amino acids and the AQC derivatizing kit which was used to make the various derivatives of AQC were obtained from commercial sources. The TLC plates were chemically bonded diphenyl-F reversed phase plates (5×20 cm, 250μ layer thickness) and were also obtained from a commercial source.

The vancomycin was first dissolved in the 0.6 m sodium chloride solution and placed in an ultrasonic bath for about 15 minutes. Then the organic modifier (acetonitrile) was added to complete the mobile phase mixture. The plates were developed at room temperature (22° C.) in 6 (i.d.)×23 cm cylindrical glass chambers. It took approximately 1–3 hours to completely develop a 5×20 cm TLC plate. All compounds were fluorescent. Spot visualization was done by using a fixed-dual wavelength (254 nm and 365 nm) ultraviolet hand lamp.

The AQC derivatives were obtained in a conventional manner, as disclosed in Pawlowska et al., J. Chromatography, Vol. 641, p. 257 (1993). Approximately 100 pmol of each isomeric compound was dissolved in 60 μL of sodium borate buffer (0.2 M, pH 8.8) in a vial and vortexed for several seconds; then 20 μL of AQC solution was added (3 mg per 1 lL of acetonitrile). The vial was heated in an oven for 10 minutes at 50° C. The resulting solutions were used in TLC without further purification.

The diphenyl-type stationary phase gave the best results in terms of low streaking and good spot integrity during development. The racemates resolved were of three types: underivatized pharmaceuticals, AQC-amino acids and dansyl amino acids. When enantiomerically pure standards were available, the retention order was determined as shown in Table XV above. The mobile phase generally consisted of between 17 and 40 volume percent acetonitrile plus 0.6 M $NaCl_{(aq)}$. The salt in the water helped to stabilize the binder on the TLC plate. Most of the racemates were better than baseline resolved. It should be noted that the retention order of all AQC-amino acids and dansyl amino acids (for which standards were available) were the same. The D-enantiomer always had a greater $R_f$ value than the L-enantiomer.

It should also be noted that besides providing good separation and enantioselectivity, the vancomycin also maintained a relatively small spot size during development.

EXAMPLE 20

This example illustrates the partial separation of optical isomers using bebeerine and a derivative of vancomycin by gas-liquid chromatography.

Using a coating solvent of ethyl ether and dichloromethane and conventional capillary gas-liquid chromatography apparatus, the vancomycin was derivatized with an n-butyl or n-hexyl isocyanate. This was done in a conventional manner. The optical isomers for which partial separation were obtained are listed in Table XVI below.

TABLE XVI

| Compound | Oven Temp. (° C.) |
|---|---|
| Vancomycin | |
| 3-chloro-2-norbornanone | 35 + 2°/min. |
| 2-ethoxy-tetrahydrofuran | 30 + 1°/min. |
| methyl-2-chloro-propionate | 35 + 1°/min. |
| β-butyro-lactone | 30 |
| 1,2-epoxyhexane | 30 + 1°/min. |
| 1-pentene-3-ol | 30 2°/min. |
| β-citronellene | 30 |
| Bebeerine | |
| α-pinene | 35 |
| α-methyl-benzyl-amine | 40 + 2°/min. |
| β-butyro-lactone | 35 + 2°/min. |

TABLE XVI-continued

| Compound | Oven Temp. (° C.) |
|---|---|
| 2-acetyl-5-norborene | 35 + 2°/min. |
| 3-chloro-butanone | 35 + 2°/min. |
| 3-methyl-cyclohexanol | 45 + 2°/min. |

Separation was accomplished in a conventional manner using conventional capillary gas-liquid chromatography. The separation, however, was only partial.

EXAMPLE 21

This example illustrates using a macrocyclic antibiotic of the present invention as a separation agent in a precipitation process.

Into a beaker containing 25 ml water and 25 ml of acetonitrile and 0.25 grams of indoprofen, the macrocyclic antibiotic vancomycin is added. Such a solution is supersaturated with the macrocyclic antibiotic by adding small portions of the organic solvent component.

The macrocyclic antibiotic complexes with indoprofen and causes a precipitate to form. The precipitate is recovered. Next, the recovered precipitate is added to water and heated to cause the complex between the macrocyclic antibiotic and indoprofen to break. The enantiomerically enriched compound is then recovered separately from the macrocyclic antibiotic. The macrocyclic antibiotic is then recovered and used again.

EXAMPLE 22

This example illustrates using a macrocyclic antibiotic, vancomycin, affixed to silica gel to obtain resolution of several racemic pyridones.

Using a conventional HPLC technique and a mobile phase of a 10/90 mix of acetonitrile and 1% triethylammonium acetate buffer at a pH of 7, the analogues which were separated into substantially pure form are reported in Table XVII below.

TABLE XVII

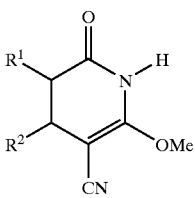

| $R^1$ | $R^2$ | Code |
|---|---|---|
| H | Me | $L_C$ |
| Ph | Ph | $L_{PhPh}$ |
| H | Ph | $L_{Ph}$ |
| Ph | H | $L_A$ |
| H | $C_6H_{11}$ | $L_{CH}$ |
| H | $CH_2Ph$ | $L_{Bz}$ |
| MeO₂C—⟨phenyl⟩—N(Me)—CH₂ | H | $L_{M1}$ |

TABLE XVII-continued

| $R^1$ | $R^2$ | Code |
|---|---|---|
| MeO₂C—⟨phenyl⟩—CH₂—CH₂ | H | $L_{M2}$ |
| $CH_3$ | H | $L_{Me}$ |

EXAMPLE 23

This example illustrates the use of rifamycin B in affinity chromatography to separate DNA polymerase from solution.

Rifamycin B is affixed to a silica gel in accordance with the present invention. A conventional liquid chromatographic column is packed with the solid support of rifamycin B bonded to the silica gel. Next, a sample containing DNA polymerase is injected into the column. The column is operated in a conventional manner using conventional equipment in order to obtain separation of the DNA polymerase.

EXAMPLE 24

This example illustrates using ristocetin A as a chiral selector in capillary electrophoresis.

Enantiomeric resolutions, migration times, and apparent and effective mobilities of enantiomers of amino acid derivatives, nonsteroidal anti-inflammatory, and carboxylic acids separated with ristocetin. The pH and concentration of ristocetin are indicated. The results are reported in Table XVIII, below.

Note this is a powerful separation technique for anions, neutral molecules. It appears to be able to resolve most N-derivatized amino acids as well. A few representative examples are shown below.

TABLE XVIII

| Compound | | Resolution | time(1)[a] | time(2)[b] | $\mu_e(1)^c$ | $\mu_e(2)^c$ |
|---|---|---|---|---|---|---|
| AQC Amino Acids[d] | | | | | | |
| Alanine | pH 7.0 | 9.4 | 8.8(D) | 12.6(L) | −2.5 | −8.0 |
| Valine | pH 7.0 | 6.0 | 10.5 | 12.6 | −5.4 | −8.0 |
| Leucine | pH 7.0 | 5.4 | 9.5(D) | 11.3(L) | −3.9 | −6.5 |
| FMOC Amino Acids[d] | | | | | | |
| Valine | pH 7.0 | 9.0 | 12.1 | 16.6 | −3.6 | −7.3 |
| Alanine | pH 7.0 | 0.4 | 14.7 | 15.0 | −6.0 | −6.2 |
| DOPS (3,4-Dihydroxy-phenylserine) | pH 7.0 | 13.8 | 11.4 | 18.6 | −2.8 | −8.4 |
| Cirtrulline | pH 7.0 | 2.6 | 9.1 | 10.0 | −1.3 | −2.8 |
| Norleucine | pH 7.0 | 0.7 | 7.4 | 7.6 | −3.1 | −3.7 |
| Serine | pH 7.0 | 2.4 | 10.9 | 12.1 | −4.2 | −5.6 |
| Dansyl Amino Acids[d] | | | | | | |
| Valine | pH 6.0 | 2.0 | 13.8 | 14.6 | −5.8 | −6.5 |
| Leucine | pH 6.0 | 3.9 | 11.3 | 15.6 | −3.3 | −7.2 |

TABLE XVIII-continued

| Compound | | Resolution | time(1)[a] | time(2)[b] | $\mu_e(1)$[c] | $\mu_e(2)$[c] |
|---|---|---|---|---|---|---|
| Aspartic acid 2,4-Dinitrophenyl Amino Acids[d] | pH 6.0 | 5.6 | 37.2(D) | 46.5(L) | −13.3 | −14.1 |
| Methionine | pH 7.0 | 7.1 | 8.2 | 11.0 | −1.0 | −6.2 |
| Norleucine[h] N-3,5-Dinitropyridyl Amino Acids[d] | pH 7.0 | 15.2 | 22.6 | 33.1 | −2.1 | −4.3 |
| Alanine[e] | pH 6.0 | 0.4 | 18.4 | 20.2 | −5.3 | −6.1 |
| Leucine Carbobenzyloxy Amino Acids[d] | pH 6.0 | 9.0 | 9.2 | 13.4 | −3.2 | −8.8 |
| Glutamic acid | pH 6.0 | 2.7 | 13.6 | 15.7 | −5.7 | −7.3 |
| Methionine PHTH-Amino Acids[d] | pH 6.0 | 8.6 | 11.1(D) | 15.2(L) | −3.0 | −6.9 |
| α-Amino-n-butyric acid | pH 6.0 | 0.1 | 14.1 | 14.5 | −6.1 | −6.4 |
| Methionine N-Benzoyl Amino Acids[d] | pH 6.0 | 2.7 | 11.7 | 13.0 | −3.8 | −5.1 |
| Methionine | pH 6.0 | 6.8 | 12.1 | 18.1 | −1.3 | −5.8 |
| Leucine N-Formyl Amino Acids[d] | pH 6.0 | 3.7 | 11.0 | 13.6 | −6.3 | −9.0 |
| Tryptophan | pH 6.0 | 5.2 | 8.1 | 10.9 | −4.9 | −6.2 |
| Phenylalanine N-Acetyl Amino Acids[d] | pH 6.0 | 0.7 | 14.0 | 14.6 | −3.9 | −4.3 |
| 4-Fluorophenylalanine | pH 7.0 | 6.7 | 8.2 | 13.5 | −1.0 | −9.0 |
| Phenylalanine Non-Steroidal Anti-inflammatory Drugs[d] | pH 6.0 | 0.6 | 14.2 | 15.0 | −4.0 | −4.6 |
| Flurbiprofen | pH 6.0 | 1.7 | 27.2 | 28.1 | −8.8 | −9.0 |
| Indoprofen | pH 6.0 | 1.3 | 12.7 | 13.1 | −4.8 | −5.2 |
| Carprofen | pH 6.0 | 1.2 | 12.1 | 12.3 | −7.4 | −7.8 |
| Ketoprofen | pH 6.0 | 5.7 | 12.3 | 14.3 | −4.4 | −6.2 |
| Suprofen Other Carboxylic Acid Compounds | pH 6.0 | 1.4 | 17.0 | 17.4 | −8.1 | −8.7 |
| 2-Phenoxypropionic acid[e] | pH 6.0 | 0.8 | 21.0 | 21.7 | −13.2 | −13.5 |
| 2-(2-Chlorophenoxy)-propionic acid[e] | pH 6.0 | 2.1 | 19.5 | 21.4 | −12.6 | −13.4 |
| Proglumide[d] | pH 6.0 | 1.5 | 14.1 | 14.5 | −9.4 | −9.8 |
| ±-Dibromohydrocinnamic acid[e] | pH 6.0 | 5.0 | 20.5 | 23.4 | −6.9 | −7.8 |
| Indolelactic acid[d] | pH 6.0 | 3.4 | 12.5 | 17.1 | −8.0 | −11.5 |
| ±-trans-4-Cotinine carboxylic acid[e] | pH 6.0 | 1.6 | 20.1 | 21.6 | −6.7 | −7.3 |
| Iopanoic acid[e] | pH 6.0 | 12.3 | 8.6 | 11.1 | −2.3 | −6.5 |
| Iophenoxic acid[e] | pH 6.0 | 12.5 | 10.9 | 13.4 | −6.2 | −9.1 |
| 2-(4-Hydroxyphenoxy)propionic acid[f] | pH 7.0 | 1.0 | 27.0 | 29.1 | −9.1 | −9.2 |
| β-Phenyllactic acid[e] | pH 6.0 | 0.7 | 16.2 | 16.8 | −4.7 | −5.1 |
| Tropic acid[e] | pH 6.0 | 0.2 | 21.4 | 21.8 | −13.4 | −13.5 |
| 3-[4-Carbonyl]- | pH 6.0 | 9.1 | 26.1 | 34.3 | −12.9 | −14.4 |
| PROXYL[d] Folinic Acid[d,i] | pH 6.0 | 1.3 | 14.8 | 16.8 | −10.0 | −11.3 |
| Atrolactic acid[e] | pH 6.0 | 0.4 | 28.6 | 29.1 | −15.3 | −15.4 |

[a]Migration time (in minutes) of the first eluting enantiomer.
[b]Migration time (in minutes) of the second eluting enantiomer.
[c]$\mu_e(1)$ and $\mu_e(2)$ are the effective electrophoretic mobilities of the first and second eluting enantiomer in $cm^2 \cdot kV^{-1} \cdot min^{-1}$.
[d]2 mM ristocetin added to run buffer.
[e]5 mM ristocetin added to run buffer.
[f]2 mM ristocetin added to run buffer with 10% 2-propanol.
[g]2 mM ristocetin added to run buffer with 20% 2-propanol.
[h]2 mM ristocetin added to run buffer with 30% 2-propanol.
[i]This is a diastereomeric separation of folinic acid.

These tests were run with a Quanta 4000 (Waters) capillary electrophoresis apparatus equipped with a fixed wavelength UV lamp. All chiral separations were performed using a 50 μm (i.d.)×32.5 cm (25 cm to detector) fused silica capillary obtained from Quadrex Corporation and detected at 254 nm. The capillary was prepared daily by conditioning with 0.1 M potassium hydroxide for 10 minutes. Next, the capillary was purged with distilled water for 5 minutes followed by the appropriate concentration and pH of the run buffer for an additional 5 minutes. The 0.1 M sodium phosphate buffer solutions were prepared in a volumetric flash and adjusted to the desired pH with sodium hydroxide. The ristocetin solution was prepared in a volumetric flask, dissolved in the appropriate phosphate buffer, and degassed by sonication. The aqueous buffer/organic modifier (2-propanol) mixture was prepared by volume. All samples were dissolved in distilled water and filtered with a 0.45 μm nylon syringe filter from Alltech prior to injection. The run voltage for all separations was +5 kV. Samples were hydrostatically injected for 3 or 5 seconds. Chiral separations were achieved with solutions of 0.1 mg/mL and at ambient temperature (22° C.). All materials used for this test were conventional.

Over 120 racemic compounds have been separated and Table XVIII lists a representative selection of those compounds that were resolved using dilute solutions of ristocetin A. This includes all types of N-blocked amino acids and a variety of other acidic or anionic compounds. Nonsteroidal anti-inflammatory compounds are particularly easy to resolve. The enantioselectivity of ristocetin A appears to be somewhat similar to that of vancomycin. However, several chiral compounds containing carboxylic acid functional groups were resolved with ristocetin A that could not be separated with vancomycin. These include: mandelic acid, 2-methoxymandelic acid, o-acetylmandelic acid, 3-methoxymandelic acid, β-phenyllactic acid, tropic acid, 2-bromo-3-methylbutyric acid, 1-benzocyclobutene-carboxylic acid and p-chloromandelic acid among others. Ristocetin A appears to be complimentary to rifamycin B and heparin (which resolve cationic compounds) when used as a CE chiral selector.

There are at least four other distinguishing features of ristocetin A-based CE separations compared to previous vancomycin-based separations. First, at all concentrations between 2 and 5 mM ristocetin A (without added organic co-solvent modifiers) the separation times were significantly less than those obtained using vancomycin. Separation times with vancomycin as a chiral selector and using analogous conditions were typically between 40 and 70 minutes. Second, as will be shown, organic modifiers can be used to substantially enhance enantioresolutions when using ristocetin A, but less so with vancomycin. Third, aqueous solutions of ristocetin A appear to decompose more slowly than those of vancomycin. Finally, the current cost of vancomycin is much less than that of ristocetin A.

EXAMPLE 25

This example illustrates the effect of ristocetin concentration on the migration times, effective mobilities, and the resolution of enantiomers. The run buffer was 0.1 M phosphate buffer, pH 6, containing the indicated concentration of ristocetin. The results are reported in Table XIX, below. These tests were run as in Example 24, above.

TABLE XIX

| Compound | Rs | t(1)[a] | t(2)[a] | t(eof)[b] | $\mu_e(1)$[c] | $\mu_e(2)$[c] |
|---|---|---|---|---|---|---|
| 2 mM Ristocetin | | | | | | |
| 2-(3-chloro-phenoxy)-propionic acid | 8.9 | 11.2 | 21.4 | 7.6 | −3.1 | −10.0 |
| Ketoprofen | 5.7 | 12.3 | 14.3 | 7.5 | −4.4 | −6.2 |
| 3-Methoxymandelic acid | 1.5 | 16.8 | 20.2 | 7.6 | −11.5 | −13.0 |
| 1-Benzocyclobutene-carboxylic acid | 1.1 | 21.0 | 22.4 | 7.5 | −13.2 | −13.7 |
| 5 mM Ristocetin | | | | | | |
| 2-(3-chloro-phenoxy)-propionic acid | 22.1 | 11.6 | 29.3 | 11.5 | −0.2 | −8.7 |
| Ketoprofen | 7.4 | 15.7 | 27.5 | 11.5 | −3.8 | −5.5 |
| 3-Methoxymandelic acid | 4.7 | 19.2 | 29.9 | 11.5 | −5.8 | −8.8 |
| 1-Benzocyclobutene-carboxylic acid | 1.8 | 42.5 | 49.6 | 11.5 | −10.3 | −10.9 |

[a]The migration times of the enantiomers, t(1) and t(2), are given in minutes
[b]The time corresponding to the electroosmotic flow, t(eof), is given in minutes. Note that a decrease in the eof velocity results in an increase in t(eof)
[c]The effective mobilities, $\mu_e(1)$ and $\mu_e(2)$ are given in cm$^2 \cdot$ kV $\cdot$ 1 min$^{-1}$.

As shown in Table XIX the concentration of ristocetin A in the run buffer can have a significant effect on the CE separation. In general, higher concentrations of the chiral selector produce higher enantioresolutions and longer separation times. The reason for the increase in analyte elution time is that higher concentrations of ristocetin tend to slow the electroosmotic flow. This is because at these pHs the positively charged ristocetin tends to interact with the wall of the capillary. Increasing the phosphate buffer concentrations lessens the wall interactions somewhat. However, there is a "trade-off" since increasing buffer concentration also increases heat generation, baseline noise and usually requires a decrease in the run voltage. The buffer concentration used throughout this project (i.e., 0.1 M phosphate) was a compromise after taking into account all of the aforementioned factors. A similar "wall-interaction effect" was previously noted for vancomycin. The wall adsorption does not seem to affect the run to run reproducibility as long as all experimental conditions are held constant.

The effective mobilities ($\mu, \epsilon$) of the analytes (which have electromigrations opposite to the direction of the electroosmotic flow) decrease with increasing concentration of ristocetin A. This is because a greater amount of the analyte is associated with the ristocetin A when the concentration of the chiral selector is increased. Hence the improvement in the enantiomeric separations at higher ristocetin A concentrations seems to be the result of two factors: (1) a greater time of association between the chiral selector and analytes due to mass action and (2) a greater time of association between the chiral selector and analyte due to the decrease in the electroosmotic flow.

EXAMPLE 26

This example illustrates the effect of pH on the migration times, effective mobilities, and resolution of enantiomers with ristocetin as a chiral selector. All separations were performed using 2 mM ristocetin in 0.1 M phosphate buffer.

Table XX, below lists the results obtained.

TABLE XX

| Compound | Rs | t(1)[a] | t(2)[a] | t(eof)[b] | $\mu_e(1)$[c] | $\mu_e(2)$[c] |
|---|---|---|---|---|---|---|
| pH 6 | | | | | | |
| 2-(3-chloro-phenoxy)-propionic acid | 8.9 | 11.2 | 21.4 | 7.6 | −3.1 | −10.0 |
| Ketoprofen | 5.7 | 12.3 | 14.3 | 7.5 | −4.4 | −6.2 |
| 3-Methoxymandelic acid | 1.5 | 16.8 | 20.2 | 7.6 | −11.5 | −13.0 |
| 1-Benzocyclobutene-carboxylic acid | 1.1 | 21.0 | 22.4 | 7.5 | −13.2 | −13.7 |
| pH 7 | | | | | | |
| 2-(3-chloro-phenoxy)-propionic acid | 5.1 | 10.1 | 13.8 | 7.5 | −4.9 | −9.2 |
| Ketoprofen | 2.6 | 12.6 | 13.7 | 7.5 | −8.1 | −9.1 |
| 3-Methoxymandelic acid | 1.1 | 18.1 | 20.2 | 7.4 | −5.8 | −6.7 |
| 1-Benzocyclobutene-carboxylic acid | 0.4 | 21.6 | 22.0 | 7.5 | −13.4 | −13.6 |

[a]The migration times of the enantiomers, t(1) and t(2), are given in minutes.
[b]The time corresponding to the electroosmotic flow, t(eof), is given in minutes. Note that a decrease in the eof velocity results in an increase in t(eof).
[c]The effective mobilities, $\mu_e(1)$ and $\mu_e(2)$ are given in cm$^2 \cdot$ kV − 1 min$^{-1}$.

These results were obtained following the procedure in Example 26, above.

Table XX shows the effect of pH on the enantioseparation of typical racemic analytes. In general, somewhat lower pHs give better enantioresolution. However, there is a limit to this effect since decreasing the pH will significantly decrease electroosmotic flow (thereby increasing analysis times) and eventually protonate the analytes making them neutral species. At sufficiently low pHs, these two effects inhibit or negate the CE enantioseparation.

EXAMPLE 27

This example illustrates the effect of concentration of 2-propanol as an organic additive on the migration times, effective mobilities and resolution of enantiomers with ristocetin as chiral selector. Table XXI lists the results below.

TABLE XXI

| Organic Solvent | Compound | $R_s$ | $t(1)^a$ | $t(2)^a$ | $t(EOF)^b$ | $\mu_e(1)^c$ | $\mu_e(2)^c$ |
|---|---|---|---|---|---|---|---|
| None | 2-(3-Chlorophenoxy)-propionic acid | 5.1 | 10.1 | 13.8 | 7.5 | 4.9 | 9.2 |
| | Ketoprofen | 2.6 | 12.6 | 13.7 | 7.5 | −8.1 | −9.1 |
| | 3-Methoxymandelic acid | 1.1 | 18.1 | 20.2 | 7.4 | −5.8 | −6.7 |
| | 1-Benzocyclobutene-carboxylic acid | 0.4 | 21.6 | 22.0 | 7.5 | −13.4 | −13.6 |
| 10% 2-Propanol | 2-(3-Chlorophenoxy)-propionic acid | 5.8 | 14.6 | 21.3 | 11.5 | −3.0 | −6.5 |
| | Ketoprofen | 4.5 | 19.6 | 21.8 | 11.5 | −5.8 | −6.7 |
| | 3-Methoxymandelic acid | 1.8 | 28.0 | 33.2 | 11.5 | −8.3 | −9.2 |
| | 1-Benzocyclobutene-carboxylic acid | 0.7 | 40.2 | 40.6 | 11.5 | −10.1 | −10.1 |
| 20% 2-Propanol | 2-(3-Chlorophenoxy)-propionic acid | 7.6 | 21.4 | 30.8 | 11.8 | −2.7 | −6.2 |
| | Ketoprofen | 5.7 | 26.3 | 29.8 | 11.8 | −7.6 | −8.4 |
| | 3-Methoxymandelic acid | 2.3 | 39.6 | 47.5 | 11.8 | −9.7 | −10.4 |
| | 1-Benzocyclobutene-carboxylic acid | 1.1 | 55.0 | 57.9 | 11.7 | −10.9 | −11.0 |
| 30% 2-Propanol | 2-(3-Chlorophenoxy)-propionic acid | 10.0 | 26.6 | 47.7 | 14.5 | −2.4 | −5.1 |
| | Ketoprofen | 5.79 | 37.6 | 43.1 | 14.6 | −4.2 | −4.8 |
| | 3-Methoxymandelic acid | 5.22 | 63.5 | 89.6 | 14.5 | −6.0 | −6.7 |
| | 1-Benzocyclobutene-carboxylic acid | 1.23 | 70.1 | 73.7 | 14.6 | −11.3 | −11.6 |

All separations were performed using 2 mM ristocetin in 0.1 M phosphate buffer (pH7) with the indicated volume percentage of organic solvent.
[a]The migration times of the enantiomers, t (1) and t (2) are given in minutes.
[b]The time corresponding to the electroosmotic flow, t (EOF), is given in minutes. Note that a decrease in the EOF velocity results in an increase in t (EOF).
[c]The effective mobilities, $\mu_e(1)$ and $\mu_e(2)$, are given in $cm^2 kV^{-1} min^{-1}$.

These results were obtained following the procedure outlined in Example 24 above.

As found in the case of another macrocyclic antibiotic (rifamycin B) the use of organic modifiers can significantly alter enantioresolution in some cases. The addition of 2-propanol to the run buffer tended to enhance enantioresolution for most analytes. Also the organic modifier greatly increased analyses (elution) times as a result of the decreasing electroosmotic flow velocity. The effect of enhancing enantioresolution with added organic modifier varies with the analyte. Eventually a level of organic modifier is reached that decreases enantioresolution. Also when using hydro-organic solvent mixtures in CE for longer periods of time, one must take precautions to prevent differential evaporation of the solution which will affect reproducibility, analysis times, resolution, etc.

Ristocetin A can decompose with time in aqueous solution. This process is accelerated at acidic or basic pHs and at elevated temperatures. For example, acid hydrolysis removes the sugars and an amine containing fragment from the molecule. Interestingly the degradation product remains active against Gram-positive bacteria. However, the overall stability of ristocetin A under typical CE operating conditions (e.g., pHs 5–7 and temperatures 15–25° C.) seems to exceed that of vancomycin. We have used solutions of ristocetin A up to 4 weeks provided they are refrigerated (~4° C.) overnight or when otherwise not in use.

EXAMPLE 28

This example illustrates that closely related macrocyclic antibiotics when used as chiral selectors have somewhat similar but not identical selectivity. In this example vancomycin is compared to teicoplanin as a chiral stationary phase. The results are listed in Table XXII, below.

TABLE XXII

| Compound | $t_1$ | $t_2$ | Column |
|---|---|---|---|
| bromacil | 9.6 | 10.6 | Van[1] |
| | 8.0 | 9.5 | Tei[2] |
| 4-phenyl-5-cyano-6-methoxy-3,4-dihydro-2-pyridone[2] | 7.9 | 8.6 | Van[3] |
| | 12.6 | 16.3 | Tei[4] |
| devrinol | 10.3 | 12.1 | Van[1] |
| | 11.6 | 12.9 | Tei[2] |
| warfarin | 9.6 | 11.6 | Van[1] |
| 3-methyl-5-cyano-6-methoxy-3,4-dihydro-2-pyridone | 5.4 | 5.8 | Van[3] |
| 4-methyl-5-cyano-6-methoxy-3,4-dihydro-2-pyridone | 9.4 | 11.0 | Van[3] |
| | 9.7 | 12.0 | Tei[4] |
| 3,4-diphenyl-5-cyano-6-methoxy-3,4-dihydro-2-pyridone | 11.4 | 12.0 | Van[3] |
| | 8.6 | 11.6 | Tei[6] |
| 4-cyclohexyl-5-cyano-6-methoxy-3,4-dihydro-2-pyridone | 15.2 | 16.2 | Van[3] |
| | 14.9 | 20.3 | Tei[4] |

[1]The column was a 25 cm × 0.44 cm (i.d.) bonded vancomycin CSP (5 μm silica gel). The mobile phase consisted of 10:90 acetonitrile-1% pH 4.1 triethylammonium acetate buffer (by volume), 1.0 ml/min.
[2]The column was a 25 cm × 0.44 cm (i.d.) bonded teicoplanin CSP (5 μm silica gel). The mobile phase was the same as the in (1), above.
[3]The column was a 25 cm × 0.44 cm (i.d.) bonded vancomycin CSP (5 μm silica gel). The mobile phase consisted of 10:90 methanol-1% pH 4.1 triethylammonium acetate buffer (by volume), 1.0 ml/min.
[4]The column was a 25 cm × 0.44 cm (i.d.) bonded teicoplanin CSP (5 μm silica gel). The mobile phase was the same as the in (3).
[5]The column was a 25 cm × 0.44 cm (i.d.) bonded vancomycin CSP (5 μm silica gel). The mobile phase consisted of 30:70 methanol-1% pH 4.1 triethylammonium acetate buffer (by volume), 1.0 ml/min.
[6]The column was a 25 cm × 0.44 cm (i.d.) bonded teicoplanin CSP (5 μm silica gel). The mobile phase was the same as the in (5).

(1) The column was a 25 cm×0.44 cm (i.d.) bonded vancomycin CSP (5 μm silica gel). The mobile phase consisted of 10:90 acetonitrile-1% pH 4.1 triethylammonium acetate buffer (by volume), 1.0 ml/min.

(2) The column was a 25 cm×0.44 cm (i.d.) bonded teicoplanin CSP (5 μm silica gel). The mobile phase was the same as that in (1), above.

(3) The column was a 25 cm×0.44 cm (i.d.) bonded vancomycin CSP (5 μm silica gel). The mobile phase consisted of 10:90 methanol-1% pH 4.1 triethylammonium acetate buffer (by volume), 1.0 ml/min.

(4) The column was a 25 cm×0.44 cm (i.d.) bonded teicoplanin CSP (5 μm silica gel). The mobile phase was the same as that in (3).

(5) The column was a 25 cm×0.44 cm (i.d.) bonded vancomycin CSP (5 μm silica gel). The mobile phase consisted of 30:70 methanol-1% pH 4.1 triethylammonium acetate buffer (by volume), 1.0 ml/min.

(6) The column was a 25 cm×0.44 cm (i.d.) bonded teicoplanin CSP (5 μm silica gel). The mobile phase was the same as that in (5).

One of the things which has been found with respect to the teicoplanin columns is that it does a good job at resolving native, underivatized amino acids and some dipeptides.

These tests were made using conventional liquid chromatography (HPLC) using identical columns except for the bonded macrocyclic antibiotic.

EXAMPLE 29

This example illustrates good results obtained using a vancomycin as a chiral stationary phase. Table XXIII lists the results.

TABLE XXIII

| Compound | $t_0$ | $K'_1$ | $K'_2$ | α | $R_s$ |
|---|---|---|---|---|---|
| Bendroflumethiazide (1) | 2.8 | 5.0 | 5.8 | 1.16 | 1.83 |
| 4-Benzl-2-oxazolidinone (2) | 2.8 | 2.46 | 3.09 | 1.26 | 1.75 |
| Bromacil (1) | 2.8 | 2.44 | 2.78 | 1.14 | 1.51 |
| Coumafuryl (3) | 2.8 | 3.13 | 4.37 | 1.4 | 2.96 |
| Devrinol (4) | 2.8 | 2.7 | 3.3 | 1.24 | 2.42 |
| Fenoterol (5) | 2.8 | 1.45 | 1.93 | 1.33 | 2.06 |
| Ketamine (1) | 2.8 | 2.97 | 3.57 | 1.20 | 2.30 |
| Luciferin (6) | 2.8 | 1.73 | 2.28 | 1.32 | 1.96 |
| Mephobarbitol (7) | 2.8 | 1.56 | 1.95 | 1.25 | 2.15 |
| 5-Methyl-5-Phenylhydanatoin (8) | 1.85 | 0.78 | 1.32 | 1.69 | 2.18 |
| 5-Methyl-5-Phenylhydanatoin (9) | 2.8 | 1.57 | 2.13 | 1.36 | 3.0 |
| Phensuximide (10) | 2.8 | 4.5 | 4.9 | 1.09 | 1.67 |
| Proglumide (11) | 2.8 | 2.31 | 3.30 | 1.43 | 3.7 |
| Pyridoglutethimide (12) | 2.8 | 2.8 | 3.3 | 1.2 | 1.8 |
| 3a,4,5,6-Tetrahydro-succinimido[3,4-b]acenaphthen-10-one (13) | 2.8 | 2.8 | 3.33 | 1.2 | 1.62 |
| Warfarin (14) | 2.8 | 2.42 | 3.14 | 1.30 | 2.57 |
| α-Methyl-benzylamine (15) | 2.8 | 3.6 | 4.2 | 1.15 | 1.47 |
| Flurbiprofen (16) | 2.8 | 2.47 | 3.23 | 1.22 | 1.95 |

Column Operating Parameters (1) Mobile Phase: 10:90 volume ration of tertrahydrofuran to 20 mM ammonium nitrate, pH 5.5
Flow Rate: 1 ml/min.
Injection Volume: 1 microliter
Sample Concentration: 2 mg/ml (2) Mobile Phase: 70:30 volume ration of hexane and ethyl alcohol
Flow Rate: 1 ml/min.
Injection Volume: 1 microliter
Sample Concentration 2 mg/ml (3) Mobile Phase: 10:90 volume ration of tetrahydrofurin to 20 mM ammonium nitrate, pH 5.5
Flow Rate: 1.2 ml/min.
Injection Volume: 1 microliter
Sample Concentration: 2 mg/ml (4) Mobile Phase: 20:80 volume ration of tetrahydrofuran to 0.1% triethylammonium acetate buffer, pH 5.
Flow Rate: 1 ml/min.
Injection Volume: 3 microliters
Sample Concentration: 2 mg/ml (5) Mobile Phase: 10:90 volume ratio of tetrahydrofuran to 20 mM ammonium nitrate, pH 5.5
Flow Rate: 1.1 ml/min.
Injection Volume: 15 microliters
Sample Concentration: 0.5 mg/ml (6) Mobile Phase: 10:90 volume ratio of tetrahydrofuran to 20 mM ammonium nitrate, pH 5.5
Flow Rate: 1.1 ml/min.
Injection Volume: 6 microliters
Sample Concentration: 0.5 mg/ml (7) Mobile Phase: 25:75 volume ratio of ethyl alcohol to hexane
Flow Rate: 1 ml/min.
Injection Volume: 30 microliters
Sample Concentration: 0.1 mg/ml (8) Mobile Phase: 100% ethyl alcohol ammonium nitrate, pH 5.5
Flow Rate: 1.5 ml/min.
Injection Volume: 5 microliters
Sample Concentration: 4 mg/ml
Column operated in normal phase (9) Mobile Phase: 90:10 volume ratio of tetrahydrofuran to 20 mM ammonium nitrate, pH 5.5
Flow Rate: 1 ml/min.
Injection Volume: 4 microliters
Sample Concentration: 3 mg/ml
Column operated in reverse phase

(10) Mobile Phase: 70:30 volume ratio of hexane to ethyl alcohol
Flow Rate: 0.5 ml/min.
Injection Volume: 10 microliters
Sample Concentration: 4 mg/ml

(11) Mobile Phase: 10:90 volume ratio of tetrahydrofuran to 20 mM ammonium nitrate, pH 5.5
Flow Rate: 1 ml/min.
Injection Volume: 3 microliters
Sample Concentration: 2 mg/ml

(12) Mobile Phase: 10:90 volume ratio of acetonitrite to 0.1% of triethylammonium acetone buffer, pH 5.5
Flow Rate: 1.1 ml/min.
Injection Volume: 15 microliters
Sample Concentration: 0.5 mg/ml

(13) Mobile Phase: 25:75 volume ratio of ethyl alcohol to hexane
Flow Rate: 1 ml/min.
Injection Volume: 1 microliter
Sample Concentration: 4 mg/ml

(14) Mobile Phase: 20:80 volume ratio of tetrahydrofuran to 0.1% triethylammonium acetone buffer, pH 5

Flow Rate: 1 ml/min.

Injection Volume: 1 microliter

Sample Concentration: 4 mg/ml

(15) Mobile Phase: 90:10 hexane to ethyl alcohol

Flow Rate: 0.5 ml/min.

Injection Volume: 1 microliter

Sample Concentration: 2 mg/ml

(16) Mobile Phase: 20:80 volume ratio of tetrahydrofuran to 20 mM ammonium nitrate, pH 5.5

Flow Rate: 1 ml/min.

Injection Volume: 2 microliters

Sample Concentration: 2 mg/ml

Column, Column Preparation and Measuring Instruments

In order to separate the different enantiomers a stationary phase of vancomycin or teichomycin and silica beads (5μ) was prepared and packed into a stainless steel column measuring 25 cm by 4.6 mm (4.4 cm inside diameter) in a conventional manner. A conventional liquid chromatograph with a UV detector (254 nm) was used to measure the separation. The columns were run in a conventional manner at room temperature (25° C.) and the chart speed was 0.5 cm/min.

EXAMPLE 30

This example illustrates separation via absorption bubble technology (e.g. flotation, foam flotation, froth flotation, floc-flotation, floc-foam flotation) using macrocyclic antibiotics in accordance with the present invention.

Figure 7:
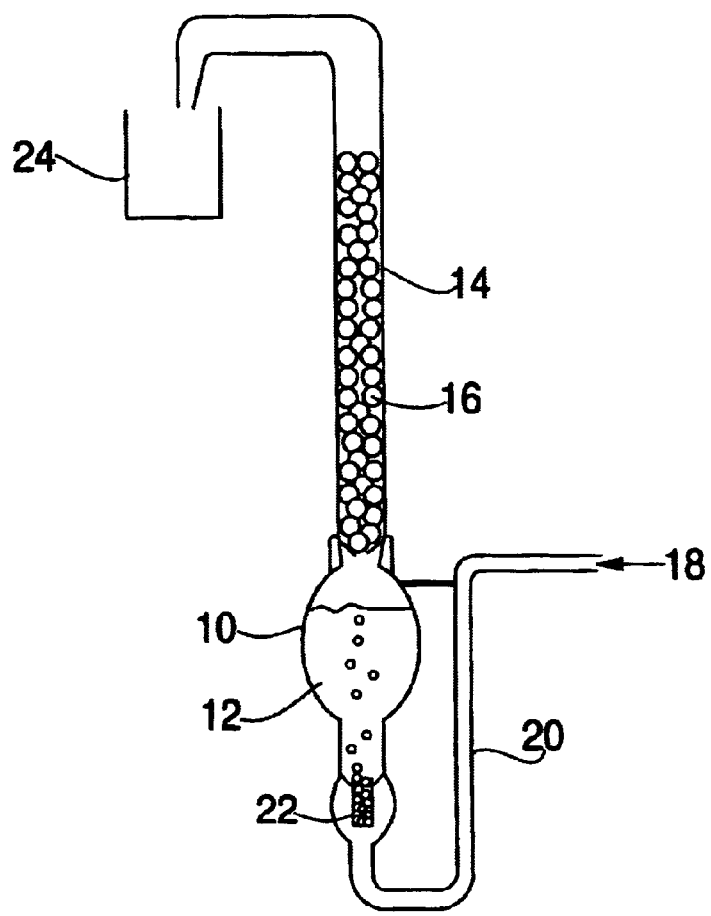
FIG. 7 illustrates a foam separation apparatus used to separate and enrich enantiomers.

Using the apparatus shown in FIG. 7, sample chamber 10 is filled with a sample and chiral separator 12. In this example, acetonitrile and vancomycin at a concentration of 12 mg/ml is diluted down to about 1% with appropriate buffer. Next, 1 mL of racemic solution and 19 mL of the dilute vancomycin solution are placed into sample chamber 10. On top of sample chamber 10 is foam column 14, which is packed with glass beads 16. Air 18 is blown through piping 20, through frit 22 and into sample chamber 10. The air bubbles passing through sample 12 cause a foam to be formed. The height of the foam is controlled by the amount of air. The foam tends to break-up as it passes through glass beads 16 and produces a thin film of liquid that flows down the column (i.e. counter current to the foam migration). After a steady counter current reflux condition is established, a foam fraction is collected in container 24 by increasing the flow rate of air 18. One of the enantiomers in the racemic solution is then collected in container 24.

The concentration of the chiral selector and racemic mixture must be optimized in each case as does pH.

In this way macrocyclic antibiotics are used to separate enantiomers using absorption bubble technology.

EXAMPLE 31

This example illustrates using Teichomycin as a chiral stationary phase.

Following the procedure in Example 29, above, Teichomycin was used as a stationary phase to separate the enantiomers identified below. The column was operated in the same manner as in Example 29 except as noted below:

D,L-Penylalanine

Mobile Phase: 40:60 volume ratio of methyl alcohol and water

Flow Rate: 1 ml/min.

Injection Volume: 1 microliter

Sample Concentration: 2 mg/ml d,l-DOPA

Mobile Phase: 40:60 volume ratio of methyl alcohol and water

Flow Rate: 1 ml/min.

Injection Volume: 1 microliter

Sample Concentration: 5 mg/ml 2.6-dimethyltyrosine

Mobile Phase: 20:80 volume ratio of ethyl alcohol to water

Flow Rate: 1 ml/min.

Injection Volume: 5 microliters

Sample Concentration: 2 mg/ml

It will be understood that the claims are intended to cover all changes and modifications of the preferred embodiments of the invention herein chosen for the purpose of illustration which do not constitute a departure from the spirit and scope of the invention.

What is claimed is:

1. A separation material for sequentially separating enantiomers from a fluid solution containing said enantiomers wherein a fluid containing said enantiomers comes in contact with said material to cause said enantiomers to sequentially separate one from another, said material being a macrocyclic antibiotic chemically bonded by a spacer to a support and said macrocyclic antibiotic is selected from the group consisting of ansamacrolides, macrolides, macrocyclic peptides, polyenes and derivatives thereof, said macrocyclic antibiotic interacting with said enantiomers to cause sequential separation by means of more than one of the following mechanisms: complexation, charge-charge interaction, hydrogen bonding, inclusion in a hydrophobic pocket, dipole stacking, or steric interaction.

2. The separation material of claim 1 wherein said support is selected from the group consisting of silica gel, alumina, polystyrenes, polyurethanes, polyvinyl alcohols, polyamides, agarose, cellulose, dextran and linear and branched amylose.

3. The separation material of claim 1 wherein said ansamacrolides are selected from the group consisting of naphthoquinoid ansamacrolides and benzoquinoid ansamacrolides and derivatives thereof.

4. The separation material of claim 3 wherein said naphthoquinoid ansamacrolides are selected from the group consisting of streptovaricins, rifamycins, tolpomycins, halomicins, naphthomycins and derivatives thereof.

5. The separation material of claim 3 wherein said benzoquinoid ansamacrolides are selected from the group consisting of geldanamycin, maytansinoids and derivatives thereof.

6. The separation material of claim 1 wherein said macrolides are selected from the group consisting of chalcomycin, methymycin, neomethymycin, erythromycin, megalomycin, picromycin, narbomycin, oleandomycin, triacetyloleandomycin, carbomycin, spiramycin, tylosin and derivatives thereof.

7. The separation material of claim 1 wherein said macrocyclic peptide is a glycopeptide or derivative thereof.

8. The separation material of claim 7 wherein said glycopeptide is selected from the group consisting of ristomycin, teichomycin, avoparcin, actaplanins, vancomycin and derivatives thereof.

9. The separation material of claim 1 wherein said macrocyclic peptides are selected from the group consisting of sporidesmolides, capreomycin, ristomycin, cyclosporins, tyrocidine, triostins, gramicidins, tyrocidines, polymyxins, bacitracins, octapeptins, actinomycins, etamycins, vernamycins, enniatins, valinomycin, thiostrepton, teichomycin, avoparcin, actaplanins, vancomycin and derivatives thereof.

10. The separation material of claim 1 wherein said polyenes are selected from the group consisting of amphotericin, candicidin, candidin, dermostatin, fungichromin, nystatin and derivatives thereof.

* * * * *